(12) United States Patent
Mori et al.

(10) Patent No.: US 11,844,352 B2
(45) Date of Patent: Dec. 19, 2023

(54) BLADDER CELL FORMATION CONTROL AGENT AND PLANT BODY INTO WHICH BLADDER CELL FORMATION CONTROL AGENT HAS BEEN INTRODUCED

(71) Applicant: Masashi Mori, Ishikawa (JP)

(72) Inventors: Masashi Mori, Ishikawa (JP); Tomohiro Imamura, Ishikawa (JP); Hiroharu Mizukoshi, Ishikawa (JP); Kanako Nishizawa, Ishikawa (JP)

(73) Assignee: Masashi Mori, Ishikawa (JP)

( * ) Notice: Subject to any disclaimer, the term of this patent is extended or adjusted under 35 U.S.C. 154(b) by 0 days.

(21) Appl. No.: 16/954,216

(22) PCT Filed: Dec. 17, 2018

(86) PCT No.: PCT/JP2018/046304
§ 371 (c)(1),
(2) Date: Sep. 18, 2020

(87) PCT Pub. No.: WO2019/124297
PCT Pub. Date: Jun. 27, 2019

(65) Prior Publication Data
US 2021/0207160 A1 Jul. 8, 2021

(30) Foreign Application Priority Data
Dec. 18, 2017 (JP) .................. 2017-242099

(51) Int. Cl.
*C12N 15/82* (2006.01)
*A01N 63/50* (2020.01)
*C07K 14/415* (2006.01)

(52) U.S. Cl.
CPC ............ *A01N 63/50* (2020.01); *C07K 14/415* (2013.01); *C12N 15/8273* (2013.01)

(58) Field of Classification Search
None
See application file for complete search history.

(56) References Cited

PUBLICATIONS

Zou et al. "A high-quality genome assembly of quinoa provides insights into the molecular basis of salt bladder-based salinity tolerance and the exceptional nutritional value". Cell Research. 27:1327-1340. Oct. 10, 2017 (Year: 2017).*
Imamura et al. "A novel WD40-repeat protein involved in formation of epidermal bladder cells in the halophyte quinoa". Communications Biology. 3(513):1-14 (Year: 2020).*
NCBI Reference Sequence: XP_021715187.1 (Year: 2017).*
Kong et al. "Identification of TaWD40D, a wheat WD40 repeat-containing protein that is associated with plant tolerance to abiotic stresses". Plant Cell Reports. 34: 395-410. (Year: 2015).*
Kennell, D.E. "Principles and practices of nucleic acid hybridization". Progress in Nucleic Acid Research and Molecular Biology. 11: 259-301 (Year: 1971).*
International Search Report and Written Opinion issued in corresponding International Patent Application No. PCT/JP2018/046304 (with English translation) dated Mar. 19, 2019 (17 pages).
Yasui et al. "Draft genome sequence of an inbred line of Chenopodium quinoa, an allotetraploid crop with great environmental adaptability and outstanding nutritional properties," Dna Research, 2016, vol. 23, No. 6, pp. 535-546.
Jarvis et al. "The genome of Chenopodium quinoa," Nature, 2017, vol. 542, pp. 307-312 (w/additional pp. 313-326).
Zou et al. "A high-quality genome assembly of quinoa provides insights into the molecular basis of salt bladder-based salinity tolerance and the exceptional nutritional value," Cell Research, 2017, vol. 27, pp. 1327-1340.
NCBI Database, No. XP_021715187, https://www.ncbi.nlm.nih.gov/protein/XP_021715187.1, Jul. 20, 2017.
Agarie et al. "Salt tolerance, salt accumulation, and ionic homeostasis in an epidermal bladder-cell less mutant of the common ice plant, *Mesembryanthemum crystallinum*," Jap. J. Crop Sci. Extra Issue, Mar. 29, 2007, vol. 223, p. 198.
Ju et al. "*Arabidopsis jingubang* Is a Negative Regulator of Pollen Germination That Prevents Pollination in Moist Environments, " The plant Cell, Sep. 2016, vol. 28, pp. 2131-2146.

* cited by examiner

*Primary Examiner* — Matthew R Keogh
*Assistant Examiner* — David R Byrnes
(74) *Attorney, Agent, or Firm* — Kilyk & Bowersox, P.L.L.C.

(57) ABSTRACT

A gene that controls epidermal bladder cell formation is isolated and identified. Specifically, a gene involved in an epidermal bladder cell formation control action is identified by: recognizing that a plant body with remarkably reduced epidermal bladder cells appears by performing EMS mutagenesis treatment on seeds; and comparing genomic DNA of the mutant and wild-type genomic DNA.

4 Claims, 7 Drawing Sheets
Specification includes a Sequence Listing.

GENE HAVING BLADDER CELL FORMATION ACTION (XM_021859495)

PROTEIN HAVING BLADDER CELL FORMATION ACTION (XP_021715187)

WD40 domain : protein interaction 35S, enhancedCaMV35S promoter; Nost, nopaline synthase terminater; rebc1, *REBC1* orf 1-300 bp region; PRO-Co, protease cofactor; HEL, NTP-binding helicase; C-PRO, cysteine protease, POL, RNA polymerase; 42KP, 42K movement protein; Vp25, Vp20 and Vp24, capsid proteins VC: VECTOR CONTROL (INDIVIDUAL INOCULATED WITH pEALSR2L5R5)

rebc1: rebc1 GENE EXPRESSION-SUPPRESSED BODY (INDIVIDUAL INOCULATED WITH pEALSR2L5R5-rebc1)

REBC1 OVEREXPRESSION VECTOR
pCAM-REBC1 (REBC1-OX)

VECTOR CONTROL
pCAM-AcGFP1 (Vector control, VC)

PLANT BODY HAVING INTRODUCED THEREIN GENE (PETIOLE PART)

BLADDER CELL FORMATION CONTROL AGENT AND PLANT BODY INTO WHICH BLADDER CELL FORMATION CONTROL AGENT HAS BEEN INTRODUCED

BACKGROUND OF THE INVENTION

1. Field of the Invention

The present invention relates to an agent having an epidermal bladder cell formation control action and a plant body having introduced therein the agent.

The present application is a National Stage Application of PCT/JP2018/046304, filed Dec. 17, 2018, which claims priority from Japanese Patent Application No. 2017-242099, which is incorporated herein by reference.

2. Description of the Related Art

Plants of the genus *Chenopodium* are known to have strong environmental stress tolerance. In recent years, quinoa of the genus *Chenopodium* has been expected to serve as a pseudocereal that can solve a world food problem because of having both a high nutritional value and strong environmental stress tolerance. Special epidermal cells (bladder cells) are considered to be involved in the environmental stress tolerance.

Arabidopsis forms tissues called trichomes, which are similar to bladder cells, on its cell surface. There is a report that, among proteins associated with the formation of the trichomes, there is a TTG1 protein having a WD40 domain (Walkeret al, Plant Cell, 1999).

SUMMARY OF THE INVENTION

The inventors of the present invention have conceived that quinoa has strong environmental stress tolerance by forming epidermal bladder cells. However, no gene that controls epidermal bladder cell formation has not been identified at all.

In view of the foregoing, an object of the present invention is to isolate and identify a gene that controls epidermal bladder cell formation.

In order to achieve the above-mentioned object, the inventors of the present invention have recognized that a plant body (mutant) with remarkably reduced epidermal bladder cells appears by performing ethyl methanesulfonate (EMS) mutagenesis treatment on seeds, and have compared genomic DNA of the mutant and wild-type genomic DNA, to thereby identify a gene involved in an epidermal bladder cell formation control action. The inventors have recognized that epidermal bladder cell formation is suppressed in a plant body having suppressed expression of a protein having an epidermal bladder cell formation action. Further, the inventors have recognized that a plant body having introduced therein a gene having an epidermal bladder cell formation action is improved in epidermal bladder cell formation action.

Thus, the inventors have completed an agent having an epidermal bladder cell formation control action according to at least one embodiment of the present invention.

That is, the present invention is as described below.

1. An agent having an epidermal bladder cell formation action, including one of a gene shown in any one of the following items (1) to (8) and a vector carrying the gene:
   (1) a gene encoding a polypeptide having an amino acid sequence set forth in SEQ ID NO: 3;
   (2) a gene encoding a polypeptide that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
   (3) a gene encoding a polypeptide that has 90% or more homology to the amino acid sequence set forth in SEQ ID NO: 3, and that has an epidermal bladder cell formation action substantially equivalent to that of the amino acid sequence set forth in SEQ ID NO: 3;
   (4) a gene formed of DNA having a base sequence set forth in SEQ ID NO: 4;
   (5) a gene formed of DNA that hybridizes with DNA having a base sequence complementary to DNA having the base sequence set forth in SEQ ID NO: 4 under stringent conditions, and that encodes a polypeptide having an epidermal bladder cell formation action;
   (6) a gene formed of DNA having a 1- to 50-base sequence substituted, deleted, inserted, and/or added in DNA having the base sequence set forth in SEQ ID NO: 4;
   (7) a gene formed of DNA having 90% or more homology to DNA having the base sequence set forth in SEQ ID NO: 4; and
   (8) the gene of at least one of the items (1) to (7) including a gene encoding a polypeptide having an amino acid sequence set forth in SEQ ID NO: 5, which is a single-base-substituted WD domain.

2. An agent having an epidermal bladder cell formation action, including a protein having an epidermal bladder cell formation action, which has an amino acid sequence of any one of the following items (1) to (4):
   (1) an amino acid sequence set forth in SEQ ID NO: 3;
   (2) an amino acid sequence that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
   (3) an amino acid sequence that has 90% or more homology to the amino acid sequence set forth in SEQ ID NO: 3, and that has an epidermal bladder cell formation action substantially equivalent to that of the amino acid sequence set forth in SEQ ID NO: 3; and
   (4) the amino acid sequence of at least one of the items (1) to (3) including an amino acid sequence set forth in SEQ ID NO: 5, which is a single-base-substituted WD domain.

3. A plant body having introduced therein the agent having an epidermal bladder cell formation action of Item 1 or 2.

4. A method of forming epidermal bladder cells in a plant body, including introducing the agent having an epidermal bladder cell formation action of Item 1 or 2 into a plant body.

5. An agent having an epidermal bladder cell formation suppression action, including one of a gene shown in any one of the following items (1) to (8) and a vector carrying the gene:
   (1) a gene encoding a polypeptide having an amino acid sequence set forth in SEQ ID NO: 1;
   (2) a gene encoding a polypeptide that has 1 to 20 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
(3) a gene encoding a polypeptide that has 90% or more homology to the amino acid sequence set forth in SEQ ID NO: 1, and that has an epidermal bladder cell formation suppression action substantially equivalent to that of the amino acid sequence set forth in SEQ ID NO: 1;
(4) a gene formed of DNA having a base sequence set forth in SEQ ID NO: 2;
(5) a gene formed of DNA that hybridizes with DNA having a base sequence complementary to DNA having the base sequence set forth in SEQ ID NO: 2 under stringent conditions, and that encodes a polypeptide having an epidermal bladder cell formation suppression action;
(6) a gene formed of DNA having a 1- to 50-base sequence substituted, deleted, inserted, and/or added in DNA having the base sequence set forth in SEQ ID NO: 2;
(7) a gene formed of DNA having 90% or more homology to DNA having the base sequence set forth in SEQ ID NO: 2; and
(8) the gene of at least one of the items (1) to (7) including a gene encoding a polypeptide having an amino acid sequence set forth in SEQ ID NO: 6, which is a single-base-substituted WD domain.
6. An agent having an epidermal bladder cell formation suppression action, including a protein having an epidermal bladder cell formation suppression action, which has an amino acid sequence of any one of the following items (1) to (4):
(1) an amino acid sequence set forth in SEQ ID NO: 1;
(2) an amino acid sequence that has 1 to 20 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
(3) an amino acid sequence that has 90% or more homology to the amino acid sequence set forth in SEQ ID NO: 1, and that has an epidermal bladder cell formation suppression action substantially equivalent to that of the amino acid sequence set forth in SEQ ID NO: 1; and
(4) the amino acid sequence of at least one of the items (1) to (3) including an amino acid sequence set forth in SEQ ID NO: 6, which is a single-base-substituted WD domain.
7. A plant body having introduced therein the agent having an epidermal bladder cell formation suppression action of Item 5 or 6.
8. A method of suppressing epidermal bladder cell formation in a plant body, including introducing the agent having an epidermal bladder cell formation suppression action of Item 5 or 6 into a plant body.
9. A use of one of a gene shown in any one of the following items (1) to (8) and a vector carrying the gene, for manufacture of an agent having an epidermal bladder cell formation suppression action:
(1) a gene encoding a polypeptide having an amino acid sequence set forth in SEQ ID NO: 1;
(2) a gene encoding a polypeptide that has 1 to 20 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
(3) a gene encoding a polypeptide that has 90% or more homology to the amino acid sequence set forth in SEQ ID NO: 1, and that has an epidermal bladder cell formation suppression action substantially equivalent to that of the amino acid sequence set forth in SEQ ID NO: 1;
(4) a gene formed of DNA having a base sequence set forth in SEQ ID NO: 2;
(5) a gene formed of DNA that hybridizes with DNA having a base sequence complementary to DNA having the base sequence set forth in SEQ ID NO: 2 under stringent conditions, and that encodes a polypeptide having an epidermal bladder cell formation suppression action;
(6) a gene formed of DNA having a 1- to 50-base sequence substituted, deleted, inserted, and/or added in DNA having the base sequence set forth in SEQ ID NO: 2;
(7) a gene formed of DNA having 90% or more homology to DNA having the base sequence set forth in SEQ ID NO: 2; and
(8) the gene of at least one of the items (1) to (7) including a gene encoding a polypeptide having an amino acid sequence set forth in SEQ ID NO: 6, which is a single-base-substituted WD domain.
10. A use of one of a gene shown in any one of the following items (1) to (8) and a vector carrying the gene, for manufacture of an agent having an epidermal bladder cell formation action:
(1) a gene encoding a polypeptide having an amino acid sequence set forth in SEQ ID NO: 3;
(2) a gene encoding a polypeptide that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) a gene encoding a polypeptide that has 90% or more homology to the amino acid sequence set forth in SEQ ID NO: 3, and that has an epidermal bladder cell formation action substantially equivalent to that of the amino acid sequence set forth in SEQ ID NO: 3;
(4) a gene formed of DNA having a base sequence set forth in SEQ ID NO: 4;
(5) a gene formed of DNA that hybridizes with DNA having a base sequence complementary to DNA having the base sequence set forth in SEQ ID NO: 4 under stringent conditions, and that encodes a polypeptide having an epidermal bladder cell formation action;
(6) a gene formed of DNA having a 1- to 50-base sequence substituted, deleted, inserted, and/or added in DNA having the base sequence set forth in SEQ ID NO: 4;
(7) a gene formed of DNA having 90% or more homology to DNA having the base sequence set forth in SEQ ID NO: 4; and
(8) the gene of at least one of the items (1) to (7) including a gene encoding a polypeptide having an amino acid sequence set forth in SEQ ID NO: 5, which is a single-base-substituted WD domain.
11. A use of a protein having an epidermal bladder cell formation suppression action, which has an amino acid sequence of any one of the following items (1) to (4), for manufacture of an agent having an epidermal bladder cell formation suppression action:

(1) an amino acid sequence set forth in SEQ ID NO: 1;
(2) an amino acid sequence that has 1 to 20 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
(3) an amino acid sequence that has 90% or more homology to the amino acid sequence set forth in SEQ ID NO: 1, and that has an epidermal bladder cell formation suppression action substantially equivalent to that of the amino acid sequence set forth in SEQ ID NO: 1; and
(4) the amino acid sequence of at least one of the items (1) to (3) including an amino acid sequence set forth in SEQ ID NO: 6, which is a single-base-substituted WD domain.

12. A use of a protein having an epidermal bladder cell formation action, which has an amino acid sequence of any one of the following items (1) to (4), for manufacture of an agent having an epidermal bladder cell formation action:
(1) an amino acid sequence set forth in SEQ ID NO: 3;
(2) an amino acid sequence that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) an amino acid sequence that has 90% or more homology to the amino acid sequence set forth in SEQ ID NO: 3, and that has an epidermal bladder cell formation action substantially equivalent to that of the amino acid sequence set forth in SEQ ID NO: 3; and
(4) the amino acid sequence of at least one of the items (1) to (3) including an amino acid sequence set forth in SEQ ID NO: 5, which is a single-base-substituted WD domain.

13. A method of suppressing epidermal bladder cell formation in a plant body, including introducing one of a gene shown in any one of the following items (1) to (8) and a vector carrying the gene into a plant body:
(1) a gene encoding a polypeptide having an amino acid sequence set forth in SEQ ID NO: 1;
(2) a gene encoding a polypeptide that has 1 to 20 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
(3) a gene encoding a polypeptide that has 90% or more homology to the amino acid sequence set forth in SEQ ID NO: 1, and that has an epidermal bladder cell formation suppression action substantially equivalent to that of the amino acid sequence set forth in SEQ ID NO: 1;
(4) a gene formed of DNA having a base sequence set forth in SEQ ID NO: 2;
(5) a gene formed of DNA that hybridizes with DNA having a base sequence complementary to DNA having the base sequence set forth in SEQ ID NO: 2 under stringent conditions, and that encodes a polypeptide having an epidermal bladder cell formation suppression action;
(6) a gene formed of DNA having a 1- to 50-base sequence substituted, deleted, inserted, and/or added in DNA having the base sequence set forth in SEQ ID NO: 2;
(7) a gene formed of DNA having 90% or more homology to DNA having the base sequence set forth in SEQ ID NO: 2; and
(8) the gene of at least one of the items (1) to (7) including a gene encoding a polypeptide having an amino acid sequence set forth in SEQ ID NO: 6, which is a single-base-substituted WD domain.

14. A method of suppressing epidermal bladder cell formation in a plant body, including introducing a protein having an epidermal bladder cell formation suppression action, which has an amino acid sequence of any one of the following items (1) to (4), into a plant body:
(1) an amino acid sequence set forth in SEQ ID NO: 1;
(2) an amino acid sequence that has 1 to 20 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
(3) an amino acid sequence that has 90% or more homology to the amino acid sequence set forth in SEQ ID NO: 1, and that has an epidermal bladder cell formation suppression action substantially equivalent to that of the amino acid sequence set forth in SEQ ID NO: 1; and
(4) the amino acid sequence of at least one of the items (1) to (3) including an amino acid sequence set forth in SEQ ID NO: 6, which is a single-base-substituted WD domain.

15. A method of forming epidermal bladder cells in a plant body, including introducing one of a gene shown in any one of the following items (1) to (8) and a vector carrying the gene into a plant body:
(1) a gene encoding a polypeptide having an amino acid sequence set forth in SEQ ID NO: 3;
(2) a gene encoding a polypeptide that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) a gene encoding a polypeptide that has 90% or more homology to the amino acid sequence set forth in SEQ ID NO: 3, and that has an epidermal bladder cell formation action substantially equivalent to that of the amino acid sequence set forth in SEQ ID NO: 3;
(4) a gene formed of DNA having a base sequence set forth in SEQ ID NO: 4;
(5) a gene formed of DNA that hybridizes with DNA having a base sequence complementary to DNA having the base sequence set forth in SEQ ID NO: 4 under stringent conditions, and that encodes a polypeptide having an epidermal bladder cell formation action;
(6) a gene formed of DNA having a 1- to 50-base sequence substituted, deleted, inserted, and/or added in DNA having the base sequence set forth in SEQ ID NO: 4;
(7) a gene formed of DNA having 90% or more homology to DNA having the base sequence set forth in SEQ ID NO: 4; and
(8) the gene of at least one of the items (1) to (7) including a gene encoding a polypeptide having an amino acid sequence set forth in SEQ ID NO: 5, which is a single-base-substituted WD domain.

16. A method of forming epidermal bladder cells in a plant body, including introducing a protein having an epidermal bladder cell formation action, which has an amino acid sequence of any one of the following items (1) to (4), into a plant body:
(1) an amino acid sequence set forth in SEQ ID NO: 3;
(2) an amino acid sequence that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) an amino acid sequence that has 90% or more homology to the amino acid sequence set forth in SEQ ID NO: 3, and that has an epidermal bladder cell formation action substantially equivalent to that of the amino acid sequence set forth in SEQ ID NO: 3; and
(4) the amino acid sequence of at least one of the items (1) to (3) including an amino acid sequence set forth in SEQ ID NO: 5, which is a single-base-substituted WD domain.

17. A plant body having suppressed expression of a protein having an epidermal bladder cell formation action, which has an amino acid sequence of anyone of the following items (1) to (4):
(1) an amino acid sequence set forth in SEQ ID NO: 3;
(2) an amino acid sequence that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) an amino acid sequence that has 90% or more homology to the amino acid sequence set forth in SEQ ID NO: 3, and that has an epidermal bladder cell formation action substantially equivalent to that of the amino acid sequence set forth in SEQ ID NO: 3; and
(4) the amino acid sequence of at least one of the items (1) to (3) including an amino acid sequence set forth in SEQ ID NO: 5, which is a single-base-substituted WD domain.

18. An agent having an epidermal bladder cell formation suppression action, including one of a nucleic acid having a partial sequence of at least 10 bases, 10 to 1,000 bases, 10 to 500 bases, 50 to 500 bases, 100 to 500 bases, 200 to 400 bases, 250 to 350 bases, or 280 to 320 bases of a base sequence of a gene shown in any one of the following items (1) to (8) and a vector carrying the nucleic acid:
(1) a gene encoding a polypeptide having an amino acid sequence set forth in SEQ ID NO: 3;
(2) a gene encoding a polypeptide that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) a gene encoding a polypeptide that has 90% or more homology to the amino acid sequence set forth in SEQ ID NO: 3, and that has an epidermal bladder cell formation action substantially equivalent to that of the amino acid sequence set forth in SEQ ID NO: 3;
(4) a gene formed of DNA having a base sequence set forth in SEQ ID NO: 4;
(5) a gene formed of DNA that hybridizes with DNA having a base sequence complementary to DNA having the base sequence set forth in SEQ ID NO: 4 under stringent conditions, and that encodes a polypeptide having an epidermal bladder cell formation action;
(6) a gene formed of DNA having a 1- to 50-base sequence substituted, deleted, inserted, and/or added in DNA having the base sequence set forth in SEQ ID NO: 4;
(7) a gene formed of DNA having 90% or more homology to DNA having the base sequence set forth in SEQ ID NO: 4; and
(8) the gene of at least one of the items (1) to (7) including a gene encoding a polypeptide having an amino acid sequence set forth in SEQ ID NO: 5, which is a single-base-substituted WD domain.

According to at least one embodiment of the present invention, the agent having an epidermal bladder cell formation control action and the plant body having introduced therein the agent can be provided.

DESCRIPTION OF THE EMBODIMENTS

Figure 1:
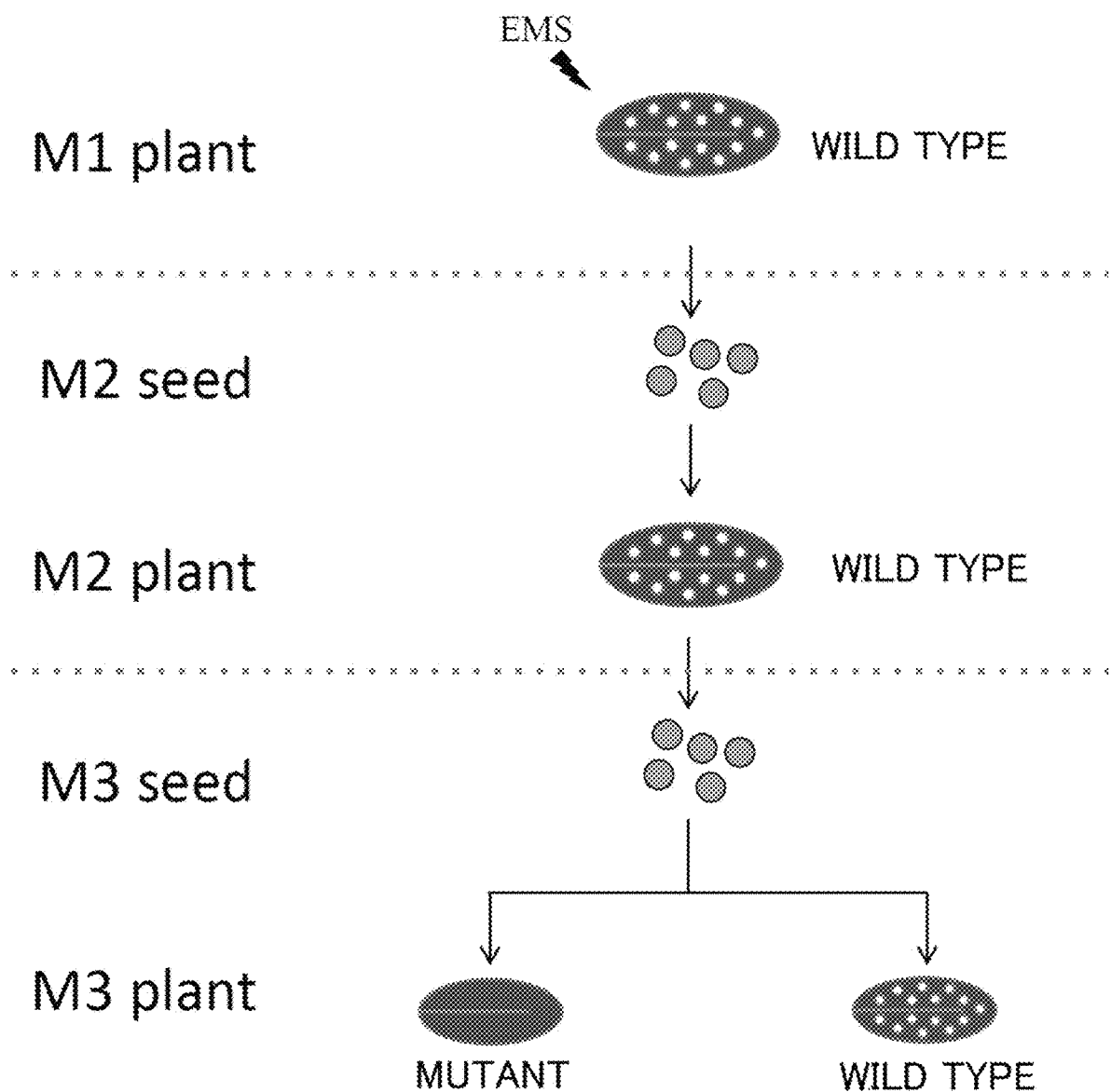
FIG. 1 is an illustration of a process of generating a plant body with remarkably reduced epidermal bladder cells by EMS mutagenesis treatment and the results thereof.

The present invention relates to an agent having an epidermal bladder cell formation control action and a plant body having introduced therein the agent. The present invention is described in detail below.

(Epidermal Bladder Cells)

Epidermal Bladder cells are spherical huge cells formed on the epidermis of plants (see Trends Plant Sci. 2014 November; 19 (11): 687-91.), and are known to accumulate salt inside themselves. Accordingly, the epidermal bladder cells are considered to be involved in salt tolerance.

(Epidermal Bladder Cell Formation Control Action)

The term "epidermal bladder cell formation control action" in at least one embodiment of the present invention means an action of controlling epidermal bladder cells of a plant body, in particular, an epidermal bladder cell formation ability action (e.g., an action of maintaining an epidermal bladder cell formation ability, an action of promoting an epidermal bladder cell formation ability, an action of increasing an epidermal bladder cell formation ability, an action of increasing the number of epidermal bladder cells to be formed, or an action of creating an epidermal bladder cell formation ability), or an epidermal bladder cell formation ability suppression action (e.g., an action of lowering an epidermal bladder cell formation ability, an action of lowering the number of epidermal bladder cells to be formed, or an action of causing the loss of an epidermal bladder cell formation ability).

(Epidermal Bladder Cell Formation Ability Suppression Action)

The epidermal bladder cell formation ability suppression action encompasses, for example, such an action that a plant body having introduced therein a gene encoding a polypeptide having the epidermal bladder cell formation suppression action according to at least one embodiment of the present invention and/or a protein having the epidermal bladder cell formation suppression action has a number of epidermal bladder cells, as compared to that of a plant body not subjected to the introduction, of 95% or less, 90% or less, 88% or less, 85% or less, 83% or less, 80% or less, 78% or less, 75% or less, 73% or less, 70% or less, 68% or less, 65% or less, 63% or less, 60% or less, 58% or less, 55% or less, 53% or less, 50% or less, 48% or less, 45% or less, 43% or less, 40% or less, 38% or less, 35% or less, 33% or less, 30% or less, 28% or less, 25% or less, 23% or less, 20% or less, 18% or less, 15% or less, 13% or less, 10% or less, 8% or less, 5% or less, 3% or less, 1% or less, or about 0%.

(Epidermal Bladder Cell Formation Ability Action)

The epidermal bladder cell formation ability action (epidermal bladder cell formation ability-promoting action) encompasses, for example, such an action that a plant body having introduced therein a gene encoding a polypeptide having the epidermal bladder cell formation action according to at least one embodiment of the present invention and/or a protein having the epidermal bladder cell formation action has a number of epidermal bladder cells, as compared to that of a plant body not subjected to the introduction, of 101% or more, 103% or more, 105% or more, 108% or more, 110% or more, 113% or more, 115% or more, 118% or more, 120% or more, 123% or more, 125% or more, 128% or more, 130% or more, 133% or more, 135% or more, 138% or more, 140% or more, 143% or more, 145% or more, 148% or more, 150% or more, 153% or more, 155% or more, 158% or more, 160% or more, 163% or more, 165% or more, 168% or more, 170% or more, 173% or more, 175% or more, 178% or more, 180% or more, 183% or more, 185% or more, 188% or more, 190% or more, 195% or more, 198% or more, 200% or more, 210% or more, 220% or more, 230% or more, 240% or more, 250% or more, 260% or more, 270% or more, 280% or more, 290% or more, 300% or more, 320% or more, 340% or more, 360% or more, 380% or more, 400% or more, 440% or more, 480% or more, 500% or more, 550% or more, 600% or more, 650% or more, 700% or more, 750% or more, 800% or more, 850% or more, 900% or more, 950% or more, 1,000% or more, 1,100% or more, 1,200% or more, 1,300% or more, 1,400% or more, 1,500% or more, 2,000% or more, 3,000% or more, 4,000% or more, 5,000% or more, 6,000% or more, 7,000% or more, 8,000% or more, 9,000% or more, 10,000% or more, or 100,000% or more.

The epidermal bladder cell formation ability action in at least one embodiment of the present invention also encompasses, in addition to the action given above as an example, an action of imparting an epidermal bladder cell formation ability to a plant having no epidermal bladder cell formation ability (action of creating an epidermal bladder cell formation ability).

(Gene Having Epidermal Bladder Cell Formation Suppression Action: Gene Encoding Polypeptide Having Epidermal Bladder Cell Formation Suppression Action)

A gene having an epidermal bladder cell formation suppression action in at least one embodiment of the present invention includes any one or more of the following genes:

(1) a gene encoding a polypeptide having an amino acid sequence set forth in SEQ ID NO: 1;

(2) a gene encoding a polypeptide that has 1 to 20 amino acids, preferably 1 to 15 amino acids, more preferably 1 to 10 amino acids, most preferably 1 to 5 amino acids substituted, deleted, inserted, and/or added in the amino acid sequence set forth in SEQ ID NO: 1, and that has an action substantially equivalent to the epidermal bladder cell formation suppression action of a polypeptide having the amino acid sequence set forth in SEQ ID NO: 1;

(3) a gene encoding a polypeptide that has 90% or more identity to the amino acid sequence set forth in SEQ ID NO: 1, and that has an action substantially equivalent to the epidermal bladder cell formation suppression action of a polypeptide having the amino acid sequence set forth in SEQ ID NO: 1;

(4) a gene formed of DNA having a base sequence set forth in SEQ ID NO: 2;

(5) a gene that hybridizes with DNA having a base sequence complementary to DNA having the base sequence set forth in SEQ ID NO: 2 under stringent conditions, and that encodes a polypeptide having an action substantially equivalent to the epidermal bladder cell formation suppression action of a polypeptide having the amino acid sequence set forth in SEQ ID NO: 1;

(6) a gene formed of DNA having a 1- to 50-base sequence substituted, deleted, inserted, and/or added in DNA having the base sequence set forth in SEQ ID NO: 2;

(7) a gene formed of DNA having 90% or more identity to DNA having the base sequence set forth in SEQ ID NO: 2; and (8) the gene of at least one of the items (1) to (7) including a gene encoding a polypeptide having an amino acid sequence set forth in SEQ ID NO: 6 (which corresponds to amino acids 139 to 432 of SEQ ID NO: 1, and in which guanine at position 380 is substituted with adenine), which is a single-base-substituted WD domain.

The gene of the above-mentioned item (2) is a gene encoding a polypeptide having introduced therein such a mutation as not to cause the epidermal bladder cell formation suppression action to be lost. Such mutation encompasses an artificial mutation as well as a naturally occurring mutation. As means for causing the artificial mutation, there may be given, for example, a site-directed mutagenesis method (Nucleic Acids Res. 10, 6487-6500, 1982). The number of mutated amino acids is generally 20 or less, preferably 10 or less, more preferably 5 or less, most preferably 3. Whether or not the polypeptide having introduced therein the mutation retains the epidermal bladder cell formation suppression action can be found by, for example, introducing a gene encoding the polypeptide having introduced therein the mutation into a plant body or the like, and checking the epidermal bladder cell formation ability of the plant body.

With regard to the gene of the above-mentioned item (3), the "action substantially equivalent to the epidermal bladder cell formation suppression action of a polypeptide having the amino acid sequence set forth in SEQ ID NO: 1" may be stronger or weaker in degree of the action as compared to the epidermal bladder cell formation suppression action of the amino acid sequence set forth in SEQ ID NO: 1. The degree of the action may be, for example, about 50%, about 60%, about 70%, about 80%, about 90%, about 100%, about 110%, about 120%, about 130%, about 140%, or about 150% as compared to the epidermal bladder cell formation suppression action of the amino acid sequence set forth in SEQ ID NO: 1.

In addition, the identity may be calculated using the Basic Local Alignment Search Tool at the National Center for Biological Information (BLAST) or the like (using, for example, default, namely initially set, parameters).

The gene of the above-mentioned item (5) is a gene obtained by utilizing hybridization between DNAs. The term "stringent conditions" in this gene refers to conditions under which only specific hybridization occurs and non-specific hybridization does not occur. Such conditions are generally conditions such as hybridization in a buffer containing 5×SSC and 1% SDS at 37° C. and washing treatment with a buffer containing 1×SSC and 0.1% SDS at 37° C., preferably conditions such as hybridization in a buffer containing 5×SSC and 1% SDS at 42° C. and washing treatment with a buffer containing 0.5×SSC and 0.1% SDS at 42° C., more preferably conditions such as hybridization in a buffer containing 5×SSC and 1% SDS at 65° C. and washing treatment with a buffer containing 0.2×SSC and 0.1% SDS at 65° C. Whether or not DNA obtained by utilizing hybridization encodes a polypeptide having activity can be found by, for example, introducing the DNA into a plant body or the like, and checking the epidermal bladder cell formation ability of the plant body. The DNA obtained by hybridization generally has high identity to the gene of the above-mentioned item (4) (SEQ ID NO: 2). The "high identity" refers to 90% or more identity, preferably 95% or more identity, more preferably 98% or more identity.

The gene of the above-mentioned item (6) is a gene formed of DNA having a 1- to 50-base sequence, preferably a 1- to 30-base sequence, more preferably a 1- to 20-base sequence, most preferably a 1- to 10-base sequence, even most preferably a 1- to 5-base sequence substituted, deleted, inserted, and/or added in DNA having the base sequence set forth in SEQ ID NO: 2.

The gene of the above-mentioned item (7) is a gene formed of DNA having 90% or more, preferably 93% or more, more preferably 95% or more, most preferably 98% or more identity to DNA having the base sequence set forth in SEQ ID NO: 2.

(Protein Having Epidermal Bladder Cell Formation Suppression Action)

A protein having an epidermal bladder cell formation suppression action in at least one embodiment of the present invention contains any one or more of the following amino acid sequences:
  (1) an amino acid sequence set forth in SEQ ID NO: 1;
  (2) an amino acid sequence that has 1 to 20, preferably 1 to 15, more preferably 1 to 10, most preferably 1 to 5 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
  (3) an amino acid sequence that has 90% or more identity to the amino acid sequence set forth in SEQ ID NO: 1, and that has an epidermal bladder cell formation suppression action substantially equivalent to that of the amino acid sequence set forth in SEQ ID NO: 1; and
  (4) the amino acid sequence of at least one of the items (1) to (3) including an amino acid sequence set forth in SEQ ID NO: 6, which is a single-base-substituted WD domain.

In the introduction of a mutation into a peptide, for example, a substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable from the viewpoint of preventing basic properties (e.g., physical properties, function, physiological activity, or immunological activity) of the peptide from being changed.

(Gene Having Epidermal Bladder Cell Formation Action: Gene Encoding Polypeptide Having Epidermal Bladder Cell Formation Action)

A gene having an epidermal bladder cell formation action in at least one embodiment of the present invention includes any one or more of the following genes:
  (1) a gene encoding a polypeptide having an amino acid sequence set forth in SEQ ID NO: 3;
  (2) a gene encoding a polypeptide that has 1 to 20 amino acids, preferably 1 to 15 amino acids, more preferably 1 to 10 amino acids, most preferably 1 to 5 amino acids substituted, deleted, inserted, and/or added in the amino acid sequence set forth in SEQ ID NO: 3, and that has an action substantially equivalent to the epidermal bladder cell formation action of a polypeptide having the amino acid sequence set forth in SEQ ID NO: 3;
  (3) a gene encoding a polypeptide that has 90% or more identity to the amino acid sequence set forth in SEQ ID NO: 3, and that has an action substantially equivalent to the epidermal bladder cell formation action of a polypeptide having the amino acid sequence set forth in SEQ ID NO: 3;
  (4) a gene formed of DNA having a base sequence set forth in SEQ ID NO: 4;
  (5) a gene that hybridizes with DNA having a base sequence complementary to DNA having the base sequence set forth in SEQ ID NO: 4 under stringent conditions, and that encodes a polypeptide having an action substantially equivalent to the epidermal bladder cell formation action of a polypeptide having the amino acid sequence set forth in SEQ ID NO: 3;
  (6) a gene formed of DNA having a 1- to 50-base sequence substituted, deleted, inserted, and/or added in DNA having the base sequence set forth in SEQ ID NO: 4;
  (7) a gene formed of DNA having 90% or more identity to DNA having the base sequence set forth in SEQ ID NO: 4; and
  (8) the gene of at least one of the items (1) to (7) including a gene encoding a polypeptide having an amino acid sequence set forth in SEQ ID NO: 5, which is a WD domain.

The gene of the above-mentioned item (2) is a gene encoding a polypeptide having introduced therein such a mutation as not to cause the epidermal bladder cell formation action to be lost. The number of mutated amino acids is generally 20 or less, preferably 10 or less, more preferably 5 or less, most preferably 3. Whether or not the polypeptide having introduced therein the mutation retains the epidermal bladder cell formation action can be found by, for example, introducing a gene encoding the polypeptide having introduced therein the mutation into a plant body or the like, and checking the epidermal bladder cell formation ability of the plant body.

In particular, the amino acid sequence set forth in SEQ ID NO: 3 contains the WD domain (SEQ ID NO: 5). When a mutation is introduced into the WD domain and/or a C-terminal region subsequent to the domain, the epidermal bladder cell formation action is highly liable to be lost, and hence it is preferred that the mutation be introduced at an amino acid outside those domains.

With regard to the gene of the above-mentioned item (3), the "action substantially equivalent to the epidermal bladder cell formation action of a polypeptide having the amino acid sequence set forth in SEQ ID NO: 3" may be stronger or weaker in degree of the action as compared to the epidermal bladder cell formation action of the amino acid sequence set forth in SEQ ID NO: 3. The degree of the action may be, for example, about 50%, about 60%, about 70%, about 80%, about 90%, about 100%, about 110%, about 120%, about 130%, about 140%, or about 150% as compared to the epidermal bladder cell formation action of the amino acid sequence set forth in SEQ ID NO: 3.

The gene of the above-mentioned item (5) is a gene obtained by utilizing hybridization between DNAs. The DNA obtained by hybridization generally has high identity to the gene of the above-mentioned item (4) (SEQ ID NO: 4). The "high identity" refers to 90% or more identity, preferably 95% or more identity, more preferably 98% or more identity.

The gene of the above-mentioned item (6) is a gene formed of DNA having a 1- to 50-base sequence, preferably a 1- to 30-base sequence, more preferably a 1- to 20-base sequence, most preferably a 1- to 10-base sequence, even most preferably a 1- to 5-base sequence substituted, deleted, inserted, and/or added in DNA having the base sequence set forth in SEQ ID NO: 4.

The gene of the above-mentioned item (7) is a gene formed of DNA having 90% or more, preferably 93% or more, more preferably 95% or more, most preferably 98% or more identity to DNA having the base sequence set forth in SEQ ID NO: 4.

(Protein Having Epidermal Bladder Cell Formation Action)

A protein having an epidermal bladder cell formation action in at least one embodiment of the present invention contains any one or more of the following amino acid sequences:

(1) an amino acid sequence set forth in SEQ ID NO: 3;
(2) an amino acid sequence that has 1 to 20, preferably 1 to 15, more preferably 1 to 10, most preferably 1 to 5 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) an amino acid sequence that has 90% or more identity to the amino acid sequence set forth in SEQ ID NO: 3, and that has an epidermal bladder cell formation action substantially equivalent to that of the amino acid sequence set forth in SEQ ID NO: 3; and
(4) the amino acid sequence of at least one of the items (1) to (3) including an amino acid sequence set forth in SEQ ID NO: 5, which is a WD domain.

(Synthesis Method for Protein Having Epidermal Bladder Cell Formation Control Action)

A protein having an epidermal bladder cell formation control action (encompassing the protein having an epidermal bladder cell formation suppression action and the protein having an epidermal bladder cell formation action) in at least one embodiment of the present invention may be synthesized using a synthesis system known per se. For example, the protein having an epidermal bladder cell formation control action in at least one embodiment of the present invention may be obtained by adding mRNA of a gene having an epidermal bladder cell formation control action in at least one embodiment of the present invention to a synthesis system known per se, such as a recombinant *Escherichia coli* protein synthesis system, an insect protein synthesis system, a yeast protein synthesis system, a plant cell protein synthesis system, or a cell-free protein synthesis system, followed by purification from a synthesis liquid as required.

(Agent Having Epidermal Bladder Cell Formation Control Action)

An agent having an epidermal bladder cell formation control action (encompassing an agent having an epidermal bladder cell formation suppression action and an agent having an epidermal bladder cell formation action) according to at least one embodiment of the present invention contains as an active ingredient any one or more of the gene having an epidermal bladder cell formation control action in at least one embodiment of the present invention, a vector carrying the gene, and the protein having an epidermal bladder cell formation control action in at least one embodiment of the present invention.

The vector in at least one embodiment of the present invention is not particularly limited as long as the vector allows the gene having an epidermal bladder cell formation control action in at least one embodiment of the present invention to be introduced into a plant body, but for example, a viral vector known per se, in particular, a plant virus vector (e.g., a vector derived from a virus belonging to the genus *Tobamovirus*, a tobacco mosaic virus vector, or a tomato mosaic virus vector) may be utilized.

In addition, an *Agrobacterium* method involving using a Ti plasmid may be utilized.

(Plant Body)

The "plant body {encompassing a callus as well as a full body}" according to at least one embodiment of the present invention is not particularly limited as long as its epidermal bladder cell formation ability is controlled through the introduction of a gene encoding a polypeptide having the epidermal bladder cell formation control action in at least one embodiment of the present invention and/or a protein having the epidermal bladder cell formation control action, but examples thereof may include a plant of the genus *Chenopodium* (e.g., quinoa, Chenopodium album var. centrorubrum, or Chenopodium album), a plant of the genus *Spinacia* (e.g., spinach), and a plant of the genus *Mesembryanthemum* (e.g., ice plant).

(Method of Introducing Gene Having Epidermal Bladder Cell Formation Control Action into Plant Body)

With regard to a method of introducing the gene having an epidermal bladder cell formation control action (encompassing the gene having an epidermal bladder cell formation suppression action and the gene having an epidermal bladder cell formation action) in at least one embodiment of the present invention into a plant body, the gene may be introduced into the plant body by a method known per se. For example, the gene having an epidermal bladder cell formation control action may be introduced into the plant body by applying a solution containing a plant virus vector carrying the gene having an epidermal bladder cell formation control action in at least one embodiment of the present invention to a leaf, a stalk, a root, an ear, or the like of the plant body.

As a method of overexpressing the gene having an epidermal bladder cell formation control action, there are given, for example, an *Agrobacterium* method, a particle gun method, a viral vector method, and a whisker method.

(Method of Introducing Protein Having Epidermal Bladder Cell Formation Control Action into Plant Body)

With regard to a method of introducing the protein having an epidermal bladder cell formation control action (encompassing the protein having an epidermal bladder cell formation suppression action and the protein having an epidermal bladder cell formation action) in at least one embodiment of the present invention into a plant body, the protein may be introduced into the plant body by a method known per se. For example, the protein having an epidermal bladder cell formation control action may be introduced into the plant body by applying a solution containing the protein having an epidermal bladder cell formation control action in at least one embodiment of the present invention to a leaf, a stalk, a root, an ear, or the like of the plant body.

Other examples of the method may include a particle gun method and an *Agrobacterium* method.

(Plant Body Having Introduced therein Gene Having Epidermal Bladder Cell Formation Suppression Action or Protein Having Epidermal Bladder Cell Formation Suppression Action)

A "plant body having introduced therein the gene having an epidermal bladder cell formation suppression action or the protein having an epidermal bladder cell formation suppression action" according to at least one embodiment of the present invention has a number of epidermal bladder cells of the whole plant, as compared to that of a wild type (plant body not having introduced therein the gene or the protein), of 90% or less, 88% or less, 85% or less, 83% or less, 80% or less, 78% or less, 75% or less, 73% or less, 70% or less, 68% or less, 65% or less, 63% or less, 60% or less, 58% or less, 55% or less, 53% or less, 50% or less, 48% or less, 45% or less, 43% or less, 40% or less, 38% or less, 35% or less, 33% or less, 30% or less, 28% or less, 25% or less, 23% or less, 20% or less, 18% or less, 15% or less, 13% or less, 10% or less, 8% or less, 5% or less, 3% or less, 1% or less, or about 0%.

Further, the "plant body having introduced therein the gene having an epidermal bladder cell formation suppression action or having introduced therein the protein having an epidermal bladder cell formation suppression action" according to at least one embodiment of the present invention is weak against an environmental stress (e.g., cultivation under high-temperature and high-humidity conditions, dryness, low temperature, ultraviolet light, or a physical stress (wind or water)) as compared to the wild type (plant body not having introduced therein the gene or the protein).

(Plant Body Having Introduced therein Gene Having Epidermal Bladder Cell Formation Action or Protein Having Epidermal Bladder Cell Formation Action)

A "plant body having introduced therein the gene having an epidermal bladder cell formation action or the protein having an epidermal bladder cell formation action" according to at least one embodiment of the present invention has a number of epidermal bladder cells of the whole plant, as compared to that of a wild type (plant body not having introduced therein the gene or the protein), of 101% or more, 103% or more, 105% or more, 108% or more, 110% or more, 113% or more, 115% or more, 118% or more, 120% or more, 123% or more, 125% or more, 128% or more, 130% or more, 133% or more, 135% or more, 138% or more, 140% or more, 143% or more, 145% or more, 148% or more, 150% or more, 153% or more, 155% or more, 158% or more, 160% or more, 163% or more, 165% or more, 168% or more, 170% or more, 173% or more, 175% or more, 178% or more, 180% or more, 183% or more, 185% or more, 188% or more, 190% or more, 195% or more, 198% or more, 200% or more, 210% or more, 220% or more, 230% or more, 240% or more, 250% or more, 260% or more, 270% or more, 280% or more, 290% or more, 300% or more, 320% or more, 340% or more, 360% or more, 380% or more, 400% or more, 440% or more, 480% or more, 500% or more, 550% or more, 600% or more, 650% or more, 700% or more, 750% or more, 800% or more, 850% or more, 900% or more, 950% or more, 1,000% or more, 1,100% or more, 1,200% or more, 1,300% or more, 1,400% or more, 1,500% or more, 2,000% or more, 3,000% or more, 4,000% or more, 5,000% or more, 6,000% or more, 7,000% or more, 8,000% or more, 9,000% or more, 10,000% or more, or 100,000% or more.

The "plant body having introduced therein the gene having an epidermal bladder cell formation action or the protein having an epidermal bladder cell formation action" according to at least one embodiment of the present invention also encompasses a case in which a wild type that originally has no epidermal bladder cell formation ability has an epidermal bladder cell formation ability.

Further, the "plant body having introduced therein the gene having an epidermal bladder cell formation action or having introduced therein the protein having an epidermal bladder cell formation action" according to at least one embodiment of the present invention is strong against an environmental stress (e.g., cultivation under high-temperature and high-humidity conditions, dryness, low temperature, ultraviolet light, or a physical stress (wind or water)) as compared to the wild type (plant body not having introduced therein the gene or the protein).

(Method of Forming Epidermal Bladder Cells in Plant Body)

A method of forming epidermal bladder cells (promoting formation thereof) in a plant body according to at least one embodiment of the present invention includes a step of introducing the gene having an epidermal bladder cell formation action and/or the protein having an epidermal bladder cell formation action into a plant body.

In addition, a method of improving the environmental stress tolerance of a plant body according to at least one embodiment of the present invention includes a step of introducing the gene having an epidermal bladder cell formation action and/or the protein having an epidermal bladder cell formation action into a plant body.

(Plant Body Having Suppressed Expression of Protein Having Epidermal Bladder Cell Formation Action)

A plant body having suppressed expression of a protein having an epidermal bladder cell formation action is a plant body having suppressed expression of a protein having an epidermal bladder cell formation action, the protein having an amino acid sequence of any one of the following items (1) to (4). Such plant body may be obtained by a method of suppressing epidermal bladder cell formation described below. The phrase "having suppressed expression of a protein" encompasses transient expression suppression and constitutive (stable) expression suppression. The plant body may be any plant without any particular limitation, and may be, for example, an angiosperm, a plant of the family Amaranthaceae, a plant of the family Poaceae, or a plant of the family Aizoaceae. The plant body is preferably a plant having a gene encoding a protein (polypeptide) having an epidermal bladder cell formation action, more preferably quinoa (*Chenopodium quinoa*).

(1) An amino acid sequence set forth in SEQ ID NO: 3;
(2) an amino acid sequence that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) an amino acid sequence that has 90% or more homology to the amino acid sequence set forth in SEQ ID NO: 3, and that has an epidermal bladder cell formation action substantially equivalent to that of the amino acid sequence set forth in SEQ ID NO: 3; and
(4) the amino acid sequence of at least one of the items (1) to (3) including an amino acid sequence set forth in SEQ ID NO: 5, which is a single-base-substituted WD domain.

(Method of Suppressing Epidermal Bladder Cell Formation)

The method of suppressing epidermal bladder cell formation can suppress epidermal bladder cell formation in a plant body of interest by suppressing the expression of the protein having an epidermal bladder cell formation action in the plant body of interest.

A method of suppressing the expression of the protein having an epidermal bladder cell formation action in the plant body of interest is not particularly limited, but examples thereof include a viral vector method, an RNAi method, the introduction of artificial microRNA, and an antisense RNA method. A method involving using an agent having an epidermal bladder cell formation suppression action described below is preferred.

(Agent Having Epidermal Bladder Cell Formation Suppression Action)

An example of the agent having an epidermal bladder cell formation suppression action may be a nucleic acid for producing double strand RNA (dsRNA) having an action of lowering, or causing the loss of, the expression of the protein having an epidermal bladder cell formation suppression action in a plant body of interest.

The nucleic acid for producing dsRNA having an action of suppressing the expression of the protein having an epidermal bladder cell formation suppression action in a plant body of interest preferably contains the base sequence of DNA having a partial sequence of the gene having an epidermal bladder cell formation action. The base sequence of DNA having a partial sequence of the gene having an epidermal bladder cell formation action may be produced by any nucleic acid synthesis method, such as PCR using primers designed on the basis of the base sequence (SEQ ID NO: 4) of the DNA of the gene. The base sequence of DNA having a partial sequence of the gene having an epidermal bladder cell formation action, which forms the nucleic acid for producing dsRNA in a plant body of interest, is preferably a base sequence having a partial sequence of at least 10 bases, 10 to 1,000 bases, 10 to 500 bases, 50 to 500 bases, 100 to 500 bases, 200 to 400 bases, 250 to 350 bases, or 280 to 320 bases of the base sequence of a gene shown in any one of the following items (1) to (8). An example of such base sequence is a base sequence of SEQ ID NO: 7.

(1) A gene encoding a polypeptide having an amino acid sequence set forth in SEQ ID NO: 3;
(2) a gene encoding a polypeptide that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) a gene encoding a polypeptide that has 90% or more homology to the amino acid sequence set forth in SEQ ID NO: 3, and that has an epidermal bladder cell formation action substantially equivalent to that of the amino acid sequence set forth in SEQ ID NO: 3;
(4) a gene formed of DNA having a base sequence set forth in SEQ ID NO: 4;
(5) a gene formed of DNA that hybridizes with DNA having a base sequence complementary to DNA having the base sequence set forth in SEQ ID NO: 4 under stringent conditions, and that encodes a polypeptide having an epidermal bladder cell formation action;
(6) a gene formed of DNA having a 1- to 50-base sequence substituted, deleted, inserted, and/or added in DNA having the base sequence set forth in SEQ ID NO: 4;
(7) a gene formed of DNA having 90% or more homology to DNA having the base sequence set forth in SEQ ID NO: 4; and
(8) the gene of at least one of the items (1) to (7) including a gene encoding a polypeptide having an amino acid sequence set forth in SEQ ID NO: 5, which is a single-base-substituted WD domain.

(Vector)

For highly efficient and long-term expression of dsRNA having an action of suppressing the expression of the protein having an epidermal bladder cell formation suppression action in cells of a plant body of interest, a method involving introduction into cells using a vector containing DNA having a partial sequence of the gene having an epidermal bladder cell formation action is preferred. An expression vector capable of expressing, in the plant body of interest, dsRNA having an action of suppressing the expression of the protein having an epidermal bladder cell formation suppression action may be preferably used as an agent having an epidermal bladder cell formation suppression action by being caused to carry DNA having a partial sequence of the gene having an epidermal bladder cell formation action. Examples of such vector include a hairpin RNA expression vector, a plant virus vector, and an RNAi vector.

The plant virus vector encompasses all kinds of vectors each capable of inducing the virus-induced gene silencing (VICS) of a target gene, and may be, for example, a tobacco rattle virus (TRV)-derived vector (pTRV) or potato virus X (PVX), and is preferably an Apple latent spherical virus (ALSV) vector containing a pEALSR2L5R5 plasmid and a pEALSR1 plasmid.

The RNAi vector encompasses all kinds of vectors each capable of expressing dsRNA of a target gene in a plant body, and may be, for example, pANDA or pHELLSGATE.

The present invention also encompasses a use of a gene shown in any one of the following items (1) to (8) or a vector carrying the gene, for manufacture of an agent having an epidermal bladder cell formation suppression action:

(1) a gene encoding a polypeptide having an amino acid sequence set forth in SEQ ID NO: 1;
(2) a gene encoding a polypeptide that has 1 to 20 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
(3) a gene encoding a polypeptide that has 90% or more homology to the amino acid sequence set forth in SEQ ID NO: 1, and that has an epidermal bladder cell formation suppression action substantially equivalent to that of the amino acid sequence set forth in SEQ ID NO: 1;
(4) a gene formed of DNA having a base sequence set forth in SEQ ID NO: 2;
(5) a gene formed of DNA that hybridizes with DNA having a base sequence complementary to DNA having the base sequence set forth in SEQ ID NO: 2 under stringent conditions, and that encodes a polypeptide having an epidermal bladder cell formation suppression action;
(6) a gene formed of DNA having a 1- to 50-base sequence substituted, deleted, inserted, and/or added in DNA having the base sequence set forth in SEQ ID NO: 2;
(7) a gene formed of DNA having 90% or more homology to DNA having the base sequence set forth in SEQ ID NO: 2; and
(8) the gene of at least one of the items (1) to (7) including a gene encoding a polypeptide having an amino acid sequence set forth in SEQ ID NO: 6, which is a single-base-substituted WD domain.

The present invention also encompasses a use of a gene shown in any one of the following items (1) to (8) or a vector carrying the gene, for manufacture of an agent having an epidermal bladder cell formation action:
(1) a gene encoding a polypeptide having an amino acid sequence set forth in SEQ ID NO: 3;
(2) a gene encoding a polypeptide that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) a gene encoding a polypeptide that has 90% or more homology to the amino acid sequence set forth in SEQ ID NO: 3, and that has an epidermal bladder cell formation action substantially equivalent to that of the amino acid sequence set forth in SEQ ID NO: 3;
(4) a gene formed of DNA having a base sequence set forth in SEQ ID NO: 4;
(5) a gene formed of DNA that hybridizes with DNA having a base sequence complementary to DNA having the base sequence set forth in SEQ ID NO: 4 under stringent conditions, and that encodes a polypeptide having an epidermal bladder cell formation action;
(6) a gene formed of DNA having a 1- to 50-base sequence substituted, deleted, inserted, and/or added in DNA having the base sequence set forth in SEQ ID NO: 4;
(7) a gene formed of DNA having 90% or more homology to DNA having the base sequence set forth in SEQ ID NO: 4; and
(8) the gene of at least one of the items (1) to (7) including a gene encoding a polypeptide having an amino acid sequence set forth in SEQ ID NO: 5, which is a single-base-substituted WD domain.

The present invention also encompasses a use of a protein having an epidermal bladder cell formation suppression action, which has an amino acid sequence of any one of the following items (1) to (4), for manufacture of an agent having an epidermal bladder cell formation suppression action:
(1) an amino acid sequence set forth in SEQ ID NO: 1;
(2) an amino acid sequence that has 1 to 20 amino acids substituted, deleted, inserted, and/or added in the amino acid sequence set forth in SEQ ID NO: 1, and that has an epidermal bladder cell formation suppression action substantially equivalent to that of the amino acid sequence set forth in SEQ ID NO: 1;
(3) an amino acid sequence that has 90% or more homology to the amino acid sequence set forth in SEQ ID NO: 1, and that has an epidermal bladder cell formation suppression action substantially equivalent to that of the amino acid sequence set forth in SEQ ID NO: 1; and
(4) the amino acid sequence of at least one of the items (1) to (3) including an amino acid sequence set forth in SEQ ID NO: 6, which is a single-base-substituted WD domain.

The present invention also encompasses a use of a protein having an epidermal bladder cell formation action, which has an amino acid sequence of any one of the following items (1) to (4), for manufacture of an agent having an epidermal bladder cell formation action:
(1) an amino acid sequence set forth in SEQ ID NO: 3;
(2) an amino acid sequence that has 1 to 20 amino acids substituted, deleted, inserted, and/or added in the amino acid sequence set forth in SEQ ID NO: 3, and that has an epidermal bladder cell formation action substantially equivalent to that of the amino acid sequence set forth in SEQ ID NO: 3;
(3) an amino acid sequence that has 90% or more homology to the amino acid sequence set forth in SEQ ID NO: 3, and that has an epidermal bladder cell formation action substantially equivalent to that of the amino acid sequence set forth in SEQ ID NO: 3; and
(4) the amino acid sequence of at least one of the items (1) to (3) including an amino acid sequence set forth in SEQ ID NO: 5, which is a single-base-substituted WD domain.

EXAMPLES

The present invention is hereinafter described in detail by way of specific examples. However, the present invention is not limited to the examples.

Example 1

(Generation of Plant Body with Remarkably Reduced Epidermal Bladder Cells by EMS Mutagenesis Treatment)

In this Example, a plant body with remarkably reduced epidermal bladder cells (alternative name: smooth mutant) was generated by EMS mutagenesis treatment in accordance with the following method.

(EMS Mutagenesis Treatment and Production of Mutant Strain)

EMS treatment of quinoa (*Chenopodium quinoa*) was performed by the following procedure. Quinoa seeds were washed with sterile water twice. After that, the seeds were shaken in a 0.2% ethyl methanesulfonate (EMS, Tokyo Chemical Industry Co., Ltd.) aqueous solution for 3 hours. After that, the aqueous solution was discarded, and the seeds were dried for from 1 day to 2 days. The seeds obtained by the mutagenesis treatment were defined as M1 seeds.

The M1 seeds obtained by the EMS treatment were sown, and were cultivated in an artificial climate chamber (23° C., humidity: 50% to 40%, light period: 12 hours, dark period: 12 hours). For each grown M1 plant body, M2 (children of M1) and M3 generations (grandchildren of M1) were grown, and at the same time, a mutant was searched for by observing phenotypes (FIG. 1).

(Recognition of Plant Body with Remarkably Reduced Epidermal Bladder Cells)

About 2,000 quinoa seeds were subjected to the EMS mutagenesis treatment and grown to the M3 generation.

Figure 2:
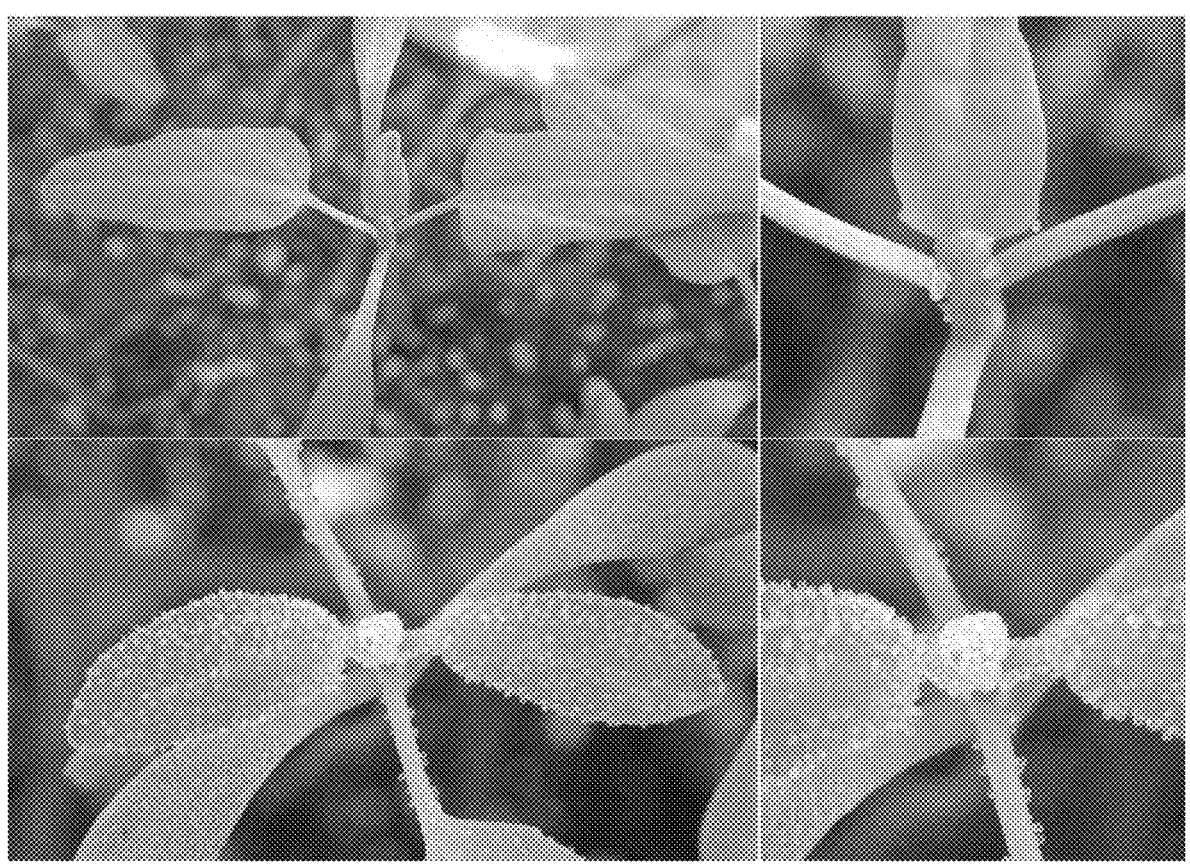
FIG. 2 includes photographs of a Reduced Epidermal Bladder Cells 1 (REBC1) mutant and a wild type.

As a result of the observation, an EMS strain in which a plant body with remarkably reduced epidermal bladder cells appeared was discovered (FIG. 2).

Figure 3:
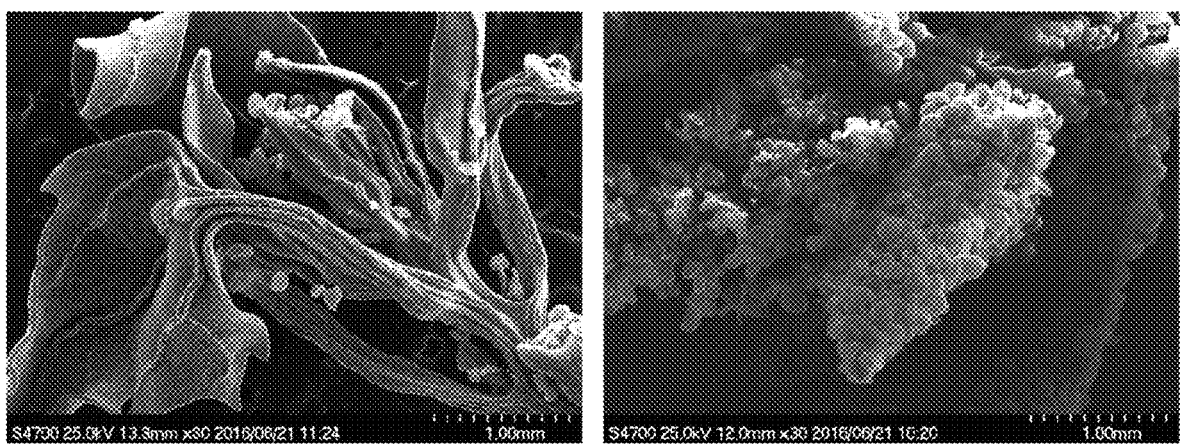
FIG. 3 includes electron micrographs of the REBC1 mutant and the wild type.

In observation using an electron microscope, the wild type had epidermal bladder cells all over the surface of a young tissue near the top of its stalk, whereas the mutant with remarkably reduced epidermal bladder cells only had a small number of epidermal bladder cells near its leaf veins (FIG. 3).

In addition, 96 individuals of the M3 generation of the mutant strain with remarkably reduced epidermal bladder cells were investigated for the numbers of individuals with the wild-type trait and individuals with the trait of remarkably reduced epidermal bladder cells, and were found to include 70 individuals of the wild type and 26 individuals with the phenotype of remarkably reduced epidermal bladder cells. According to the results, a segregation ratio between the wild type and the phenotype of remarkably reduced epidermal bladder cells was 3:1, recognizing that the trait of remarkably reduced epidermal bladder cells was a recessive trait in single-gene dominance.

Example 2

(Isolation of Gene Involved in Epidermal Bladder Cell Formation Control and Generation of Plant Body Having Introduced Therein the Gene)

In this Example, a gene involved in epidermal bladder cell formation control was isolated, and further, a plant body having introduced therein the isolated gene was generated.

(Isolation of Gene Involved in Epidermal Bladder Cell Formation Control)

The result of the segregation ratio of Example 1 revealed that one gene was involved in epidermal bladder cell formation control.

In view of this, the base sequence of the gene involved in epidermal bladder cell formation control was identified.

With regard to the EMS strain in which the phenotype of remarkably reduced epidermal bladder cells appeared in Example 1, in order to isolate the gene involved in epidermal bladder cell formation control, 25 individuals of the M3 plant bodies showing the phenotype of remarkably reduced epidermal bladder cells and 25 individuals of the M3 plant bodies showing the wild-type trait were sampled, and the individuals with each trait were subjected to the extraction of genomic DNA in one batch. The base sequence of the extracted genomic DNA was analyzed by an analysis method involving using a next-generation sequencer (HiSeqX10, Illumina, Inc.) (see Akagi, T., Henry, I. M., Tao, R. and Comai, L. 2014, Plant genetics. AY-chromosome-encoded small RNA acts as a sex determinant in persimmons. Science, 346, 646-50.).

Figure 4:
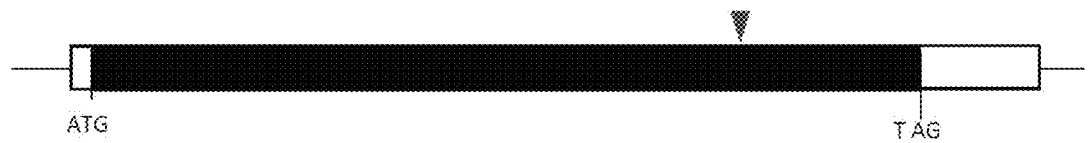
FIG. 4 is an illustration of a gene involved in epidermal bladder cell formation control.
Figure 4:
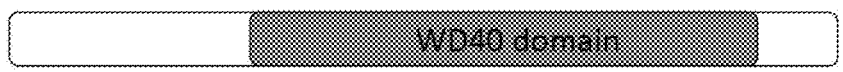

As a result of the analysis, a gene encoding a protein of unknown function having a WD40 domain (FIG. 4: Accession No. XM_021859495, SEQ ID NO: 4) was obtained as a candidate.

The protein of unknown function having a WD40 domain (Acc. No. XP_021715187, SEQ ID NO: 3) was a protein having a full length of 482 amino acid residues and having a WD40 domain in a region of amino acid residues 139 to 432 (base sequence: SEQ ID NO: 4). This gene was named REBC1 gene.

Arabidopsis forms tissues called trichomes, which are similar to epidermal bladder cells, on its cell surface. There is a report that, among proteins associated with the formation of the trichomes, there is a TTG1 protein having a WD40 domain (Walker, A. R., Davison, P. A., Bolognesi-Winfield, A. C., et al. 1999, The TRANSPARENTTESTA GLABRA1 locus, which regulates trichome differentiation and anthocyanin biosynthesis in Arabidopsis, encodes a WD40 repeat protein. Plant Cell, 11, 1337-50.). The TTG1 protein and the protein encoded by the REBC1 gene were compared for homology, and their homology was found to be 24%, recognizing that the proteins were different from each other.

In addition, it was recognized that, in the plant body showing the phenotype of remarkably reduced epidermal bladder cells obtained by EMS treatment, guanine (G) at position 1139 of the REBC1 gene had been changed to adenine (A) to change tryptophan (Trp) as amino acid 380 to a STOP (FIG. 4, base sequence: SEQ ID NO: 2).

(Generation of Plasmid for Suppressing Expression of Gene Involved in Epidermal Bladder Cell Formation Control)

Figure 5:
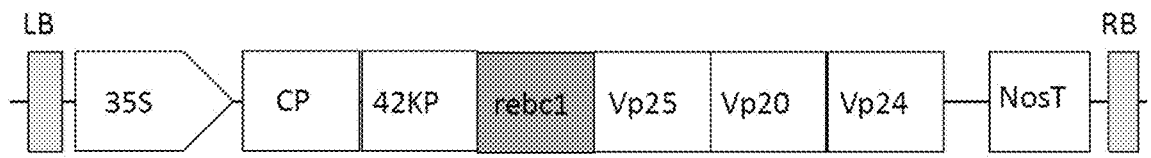
FIG. 5 is an illustration of a plasmid for suppressing the expression of the gene involved in epidermal bladder cell formation control.
Figure 5:
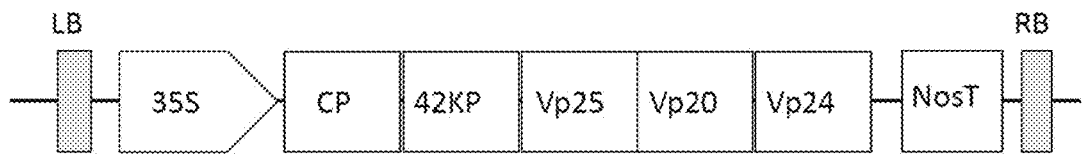
Figure 5:

A fragment in which restriction enzymes XhoI and BamHI were added to the 5' and 3' ends of the ORF region (1-300 bp: SEQ ID NO: 7) of the REBC1 gene was synthesized by PCR. Then, the resultant PCR fragment was cleaved with XhoI and BamHI, and inserted into the XhoI and BamHI sites of pEALSR2L5R5 (see Li, C., Sasaki, N., Isogai, M. and Yoshikawa, N. 2004, Stable expression of foreign proteins in herbaceous and apple plants using Apple latent spherical virus RNA2 vectors. Arch. Virol., 149, 1541-58.) to give pEALSR2L5R5-REBC1 (FIG. 5).

(Generation of Plant Body Having Suppressed Expression of Gene Involved in Epidermal Bladder Cell Formation Control Through Use of Viral Vector)

In order to prove the isolated gene to be a gene involved in epidermal bladder cell formation control, a plant body having introduced therein REBC1 was generated using a plant virus vector (see Li, C., Sasaki, N., Isogai, M. and Yoshikawa, N. 2004, Stable expression of foreign proteins in herbaceous and apple plants using Apple latent spherical virus RNA2 vectors. Arch. Virol., 149, 1541-58.), and was evaluated for the number of epidermal bladder cells.

Specifically, a solution of a pEALSR2L5R5-REBC1 plasmid having cloned therein a fragment of the REBC1 gene was mixed with an equal amount of a pEALSR1 plasmid (see Li, C., Sasaki, N., Isogai, M. and Yoshikawa, N. 2004, Stable expression of foreign proteins in herbaceous and apple plants using Apple latent spherical virus RNA2 vectors. Arch. Virol., 149, 1541-58.) solution, and carborundum was further added to generate a mixed liquid containing a vector pEALSR2L5R5-rebc1 obtained by introducing a fragment (rebc1) having a sequence of bases 1 to 300 of the REBC1 gene (SEQ ID NO: 4) into the viral vector. As a vector control, pEALSR2L5R5 (FIG. 5) was used. Those mixed liquids were applied to green leaves of wild-type quinoa, and the plant body was grown. The plant body after 1 month from the inoculation was observed to determine the presence or absence of epidermal bladder cells.

Figure 6:
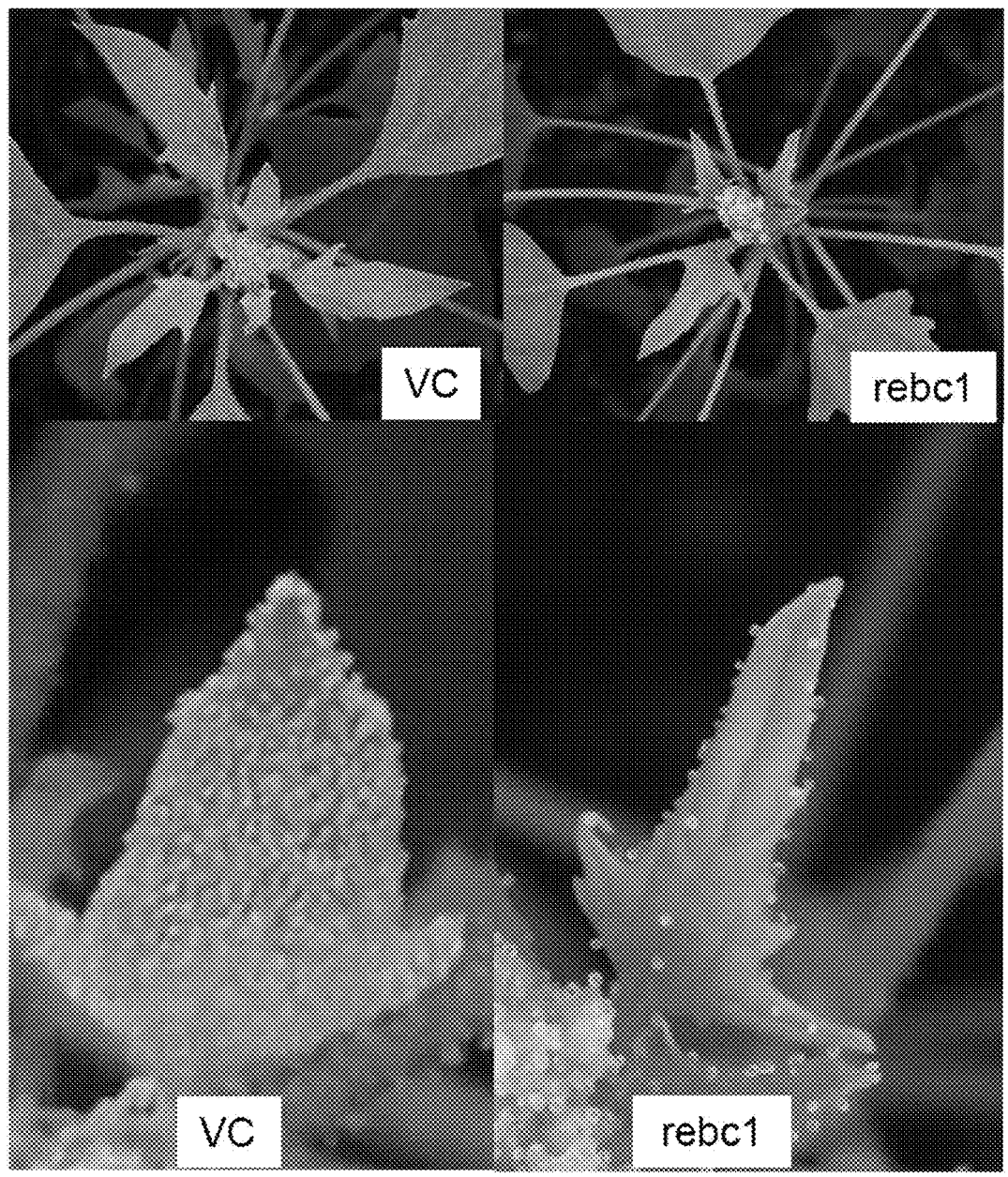
FIG. 6 includes photographs of a plant body having introduced therein the plasmid for suppressing the expression of the gene involved in epidermal bladder cell formation control.

The results showed that epidermal bladder cell formation was remarkably suppressed in the plant body inoculated with pEALSR2L5R5-rebc1 (FIG. 6).

Thus, it was recognized that the isolated REBC1 gene (base sequence: SEQ ID NO: 4) was a gene involved in epidermal bladder cell formation control.

It was also recognized that the mutation of guanine (G) at position 1139 of the REBC1 gene to adenine (A) (base sequence: SEQ ID NO: 2) resulted in the phenotype of remarkably reduced epidermal bladder cells.

Example 3

(Investigation of Environmental Stress Tolerance)

In this Example, the environmental stress tolerance of a plant body having the base sequence (SEQ ID NO: 2) in which guanine (G) at 1139 of the REBC1 gene had been mutated to adenine (A) was investigated.

In the same manner as in Example 2, 100 M3 seeds of the EMS strain (REBC1 mutant) in which the phenotype of remarkably reduced epidermal bladder cells appeared in Example 1 were sown, and then cultivated under normal conditions for 3 weeks. The resultant plant bodies were cultivated under high-temperature and high-humidity (30° C. to 32° C. (light period), 23° C. (dark period), humidity: 100%, light period: 12 hours, dark period: 12 hours) conditions for 1 month. The growth states of the plant bodies were observed.

(Results of Environmental Stress Tolerance)

Figure 7:
FIG. 7 includes photographs of the REBC1 mutant and the wild type in an environmental stress tolerance test.

The results of cultivation of the REBC1 mutant and the wild type under high-temperature and high-humidity conditions were as described below. 38 individuals out of a total of 40 individuals of the REBC1 mutant had sustained serious injury near the top of the stalk (FIG. 7). Meanwhile, the injury found in the REBC1 mutant was not found in any of a total of 56 individuals of the wild type (FIG. 7).

Thus, it was revealed that the gene involved in epidermal bladder cell formation control was involved in the improvement or lowering of the protective function of epidermal bladder cells against a stress on the plant.

Example 4

(Stress Tolerance of Plant Body Having Introduced therein Gene Having Epidermal Bladder Cell Formation Action)

In this Example, the function of the gene having an epidermal bladder cell formation action obtained in Example 2 was investigated. In addition, it is determined whether or not a plant body having introduced therein the gene has stress tolerance. Details are as described below.

(Generation of Plasmid Overexpressing Gene Having Epidermal Bladder Cell Formation Action)

A fragment in which restriction enzymes EcoRI and BamHI were added to the 5' and 3' ends of the full-length ORF of REBC1 gene set forth in SEQ ID NO: 4 was synthesized by PCR. Then, the resultant PCR fragment was cleaved with EcoRI and BamHI, and inserted into EcoRI and BamHI sites present downstream of the constitutive expression CaMV35S promoter of pCAMBIA1301M (Imamura et al, Plant Cell Physiol, 2007). The resultant vector was named pCAMBIA-REBC1-ox. In addition, pCAMBIA1301M was used as a vector control.

(Investigation of Function of Gene Having Epidermal Bladder Cell Formation Action)

Figure 8:
FIG. 8 includes an illustration of an REBC1 gene expression plasmid and photographs of a plant body having introduced therein the plasmid (overexpression).
Figure 8:
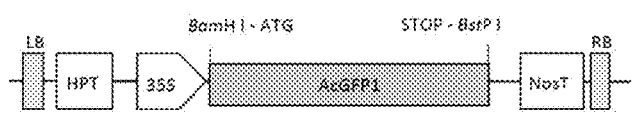
Figure 8:
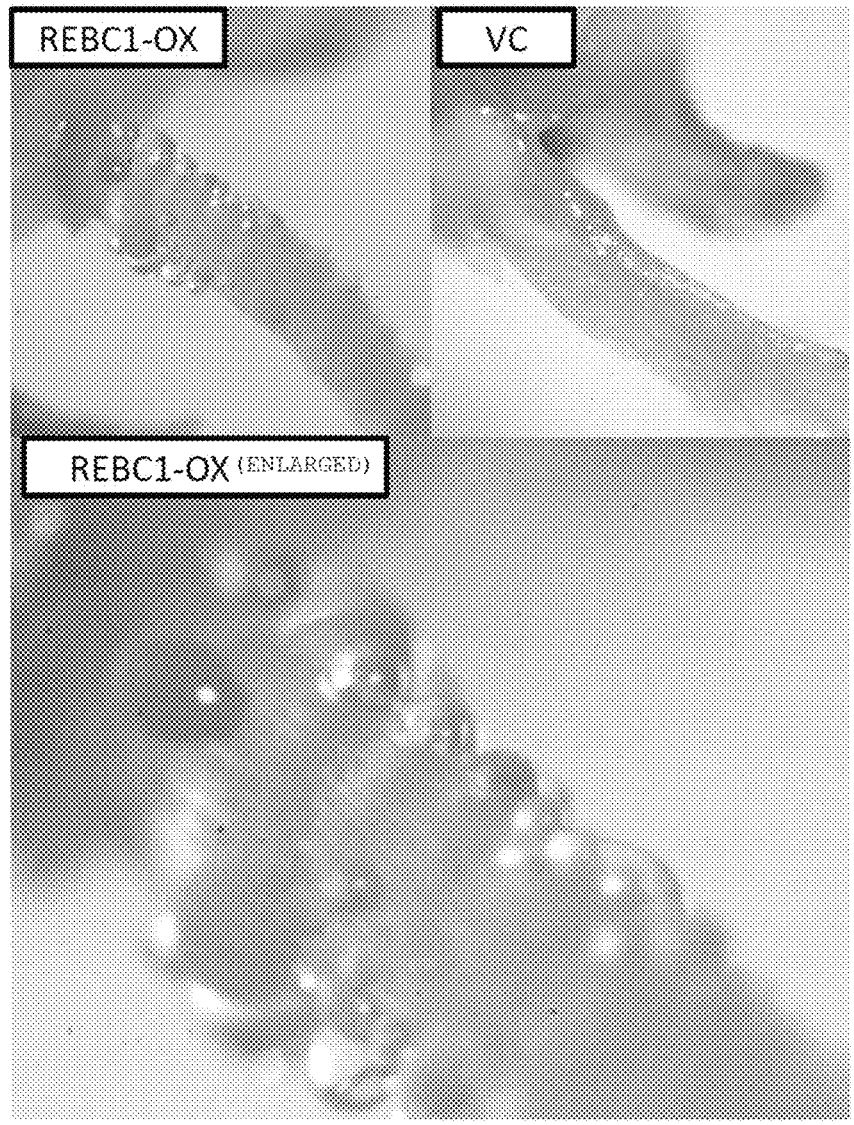

A complementary experiment was performed as to whether the isolated gene set forth in SEQ ID NO: 4 had an ability to recover from the REBC1 mutation. Specifically, for the REBC1 mutant, quinoa overexpressing the REBC1 gene set forth in SEQ ID NO: 4 was generated by a method involving using *Agrobacterium* (FIG. 8).

The number of epidermal bladder cells formed on the petiole tissue surface of the resultant plant body was measured. In the body overexpressing the REBC1 gene set forth in SEQ ID NO: 4, the formation of epidermal bladder cells was recognized after the introduction of the gene at the site (petiole) where epidermal bladder cells had not been formed before the introduction of the gene. Meanwhile, in a plant having introduced therein the vector control (FIG. 8), the induction of epidermal bladder cell formation was not found. Thus, it was revealed that the REBC1 gene set forth in SEQ ID NO: 4 (gene having an epidermal bladder cell formation action) had an epidermal bladder cell formation action (action of promoting an epidermal bladder cell formation ability, action of maintaining an epidermal bladder cell formation ability, action of increasing an epidermal bladder cell formation ability, action of increasing the number of bladder cells to be formed, or action of creating an epidermal bladder cell formation ability).

(Stress Tolerance Test of Plant Body)

Innumerable epidermal bladder cells are generally formed on the surface of a wild-type callus (dedifferentiated cells). Meanwhile, only a small number of epidermal bladder cells are formed on a callus of the REBC1 mutant generated in Example 2. On the basis of this finding, in this Example, the number of formed epidermal bladder cells present on the surface of the callus is measured to evaluate the epidermal bladder cell formation ability (-promoting) action of a plant body based on the introduction of the gene having an epidermal bladder cell formation action.

Specifically, transformed *Rhizobium rhizogenes* harboring the overexpression plasmid (pCAMBIA-REBC1-ox) or the vector control (pCAMBIA1301M) is used to introduce the overexpression plasmid (pCAMBIA-REBC1-ox) or the vector control (pCAMBIA1301M) into the REBC1 mutant (Ron et al, Plant Physiol, 2014). Quinoa into which, by such introduction, the gene having an epidermal bladder cell formation action had been introduced, formed hairy roots. A callus was induced from the hairy roots, and the number of epidermal bladder cells formed on the surface thereof was evaluated.

Further, the resultant callus is cultured in a medium containing NaCl, and an ability to tolerate salt is evaluated on the basis of a proliferative capacity or a survival rate. In addition, the concentration of salt contained in the epidermal bladder cells of the cultured callus is also measured.

(Stress Tolerance of Plant Body Having Introduced Therein Gene Having Epidermal Bladder Cell Formation Action)

The callus overexpressing the gene having an epidermal bladder cell formation action is cultured in a medium containing NaCl to recognize that more living individuals are obtained as compared to a control. Further, for epidermal bladder cells subjected to stress treatment, the composition of the contents thereof is measured to recognize the accumulation of salt at high concentration.

Therefore, the presence of many epidermal bladder cells in a plant body shows tolerance to a salt stress.

The plasmid (pCAMBIA-REBC1-ox) overexpressing the gene having an epidermal bladder cell formation action is introduced into a wild type to generate a body overexpressing a protein having an epidermal bladder cell formation action. It is recognized that the overexpressing plant, as compared to the wild type, has epidermal bladder cells excessively formed in tissues that originally have small numbers of epidermal bladder cells (stalk and mature leaves). The resultant transformant and the wild type are subjected to salt and dryness stress tests to recognize that the overexpressing body has higher stress tolerance than the wild type.

Therefore, the plant body having introduced therein the gene having an epidermal bladder cell formation action has higher stress tolerance than the wild type.

According to at least one embodiment of the present invention, the agent having an epidermal bladder cell formation control action and the plant body having introduced therein the agent can be provided.

---

What is claimed is:

1. A method of forming epidermal bladder cells in a plant body, including introducing one of a gene shown in any one of the following items (1) to (4) and a vector carrying the gene, or a protein having an epidermal bladder cell formation action, which has an amino acid sequence of any one of the following items (5) to (6), into a plant body of a genus *Chenopodium*, *Spinacia*, or *Mesembryanthemum*:
   (1) a gene encoding a polypeptide having the amino acid sequence of SEQ ID NO: 3;
   (2) a gene encoding a polypeptide that has 90% or more identity to the amino acid sequence set forth in SEQ ID NO: 3, and that has 50% or more of an epidermal bladder cell formation action compared to that of the amino acid sequence set forth in SEQ ID NO: 3;
   (3) a gene having the sequence set forth in SEQ ID NO: 4;
   (4) a gene that has 98% or more identity with DNA having the base sequence set forth in SEQ ID NO: 4, and that encodes a polypeptide having an epidermal bladder cell formation action;
   (5) the amino acid sequence of SEQ ID NO: 3; and
   (6) an amino acid sequence that has 90% or more identity to the amino acid sequence set forth in SEQ ID NO: 3, and that has 50% or more of an epidermal bladder cell formation action compared to that of the amino acid sequence set forth in SEQ ID NO: 3.

2. The method of forming epidermal bladder cells in a plant body according to claim 1, wherein the gene or the vector carrying the gene is selected from any one of the following items (1) to (4):
   (1) a gene encoding a polypeptide having the amino acid sequence of SEQ ID NO: 3;
   (2) a gene encoding a polypeptide that has 90% or more identity to the amino acid sequence set forth in SEQ ID NO: 3, and that has 50% or more of an epidermal bladder cell formation action compared to that of the amino acid sequence set forth in SEQ ID NO: 3;
   (3) a gene having the sequence set forth in SEQ ID NO: 4; and
   (4) a gene having 98% or more identity to DNA having the base sequence set forth in SEQ ID NO: 4, and that encodes a polypeptide having an epidermal bladder cell formation action.

3. The method of forming epidermal bladder cells in a plant body according to claim 1, wherein the gene or the vector carrying the gene is selected from any one of the following items (1) to (2):
   (1) a gene encoding a polypeptide having the amino acid sequence of SEQ ID NO: 3; and
   (2) a gene having the sequence set forth in SEQ ID NO: 4.

4. A plant body having enhanced expression of a protein having an epidermal bladder cell formation action, which has an amino acid sequence of any one of the following items (1) to (2):
   (1) the amino acid sequence of SEQ ID NO: 3; and
   (2) an amino acid sequence that has 90% or more identity to the amino acid sequence set forth in SEQ ID NO: 3, and that has 50% or more of an epidermal bladder cell formation action compared to that of the amino acid sequence set forth in SEQ ID NO: 3, wherein
   the plant body is of a genus *Chenopodium*, *Spinacia*, or *Mesembryanthemum*.

* * * * *

```
                        SEQUENCE LISTING

<160> NUMBER OF SEQ ID NOS: 7

<210> SEQ ID NO 1
<211> LENGTH: 379
<212> TYPE: PRT
<213> ORGANISM: Chenopodium quinoa

<400> SEQUENCE: 1

Met His Ala His Thr Lys Ile Ser Leu Val His Ile Ser Thr Pro Val
1               5                   10                  15

Phe Ser Leu Ala Met Asp Arg Gln Leu Ser His Lys Lys Ser Leu Ser
                20                  25                  30

Cys Phe Phe Asp Glu Asp Phe Thr Glu Asp Gln Ser Pro Ser Phe Gln
            35                  40                  45

His Leu Ser Lys His Asn Gln Asn Phe Leu Ala Arg Leu His Gly Thr
        50                  55                  60

His Phe Tyr Pro Asp Thr Ser Pro Met Met Ser Gln Ser Pro Glu Ser
65                  70                  75                  80

Ser Trp Ser Pro Ser Pro Ser Leu Thr Pro Ser His Pro Ser Leu Leu
                85                  90                  95

Tyr Cys Cys Ile Ser Ser Leu Arg Arg Asp Gly Asp Ile Tyr Ser Leu
                100                 105                 110

Thr Val Phe Gly Asp Leu Val Leu Thr Gly Ser Ser Ser Arg Arg Val
            115                 120                 125

Tyr Ala Trp Gln Ser Leu Asp Cys His Ala Lys Gly Tyr Ile Gln Ser
        130                 135                 140

Ser Ser Gly Glu Val Arg Ala Met Gln Val Tyr Asp Asp Met Leu Phe
145                 150                 155                 160

Thr Ala His Lys Asp His Lys Ile Arg Ile Trp Asn Met Arg Thr Cys
                165                 170                 175

Ser Gly Ser Phe Arg Ala Arg Lys Val Leu Thr Leu Pro Cys Ala Ser
                180                 185                 190

His Phe Lys Ser Phe Ile Cys Arg Ser Val Val Pro His His Arg Leu
            195                 200                 205

Thr Ala Asn Lys Pro Ile Thr Pro Gln His Arg Asp Ile Ile Ser Cys
        210                 215                 220

Met Ala Phe Tyr Tyr Val Glu Ser Ile Leu Tyr Thr Gly Ser Phe Asp
225                 230                 235                 240

Lys Thr Ile Lys Ala Trp Lys Leu Ser Val Lys Lys Cys Ile Asp Ser
                245                 250                 255

Phe Val Ala His Gly Asp His Ile Asn Asp Met Val Val Asn Gln Gln
                260                 265                 270

Ser Gly Tyr Leu Phe Thr Cys Ser Ser Asp Gly Thr Val Lys Met Trp
            275                 280                 285

Leu Arg Val Tyr Gly Glu His Ser His Val Leu Ile Lys Val Phe Ser
        290                 295                 300

Phe His Thr Tyr Pro Ile Tyr Ala Leu Ala Leu Gly Val Ser Pro Ser
305                 310                 315                 320

Gln Arg Ser Phe Leu Tyr Ser Gly Ser Ser Asp Gly Cys Ile Asn Phe
                325                 330                 335

Trp Val Gln Glu Ile Ser Thr His Tyr Asn His Gly Gly Val Leu Glu
                340                 345                 350
```

```
Gly His Gln Phe Ala Val Leu Cys Leu Val Thr Leu Asp Asn Leu Val
        355                 360                 365

Ile Ser Gly Ser Glu Asp Ser Thr Ile Arg Ile
    370                 375

<210> SEQ ID NO 2
<211> LENGTH: 1140
<212> TYPE: DNA
<213> ORGANISM: Chenopodium quinoa

<400> SEQUENCE: 2
atgcacgcac acacaaagat ttccctagtt cacatctcca ctcctgtttt ttctcttgcg      60
atggatcgcc agctcagtca caagaaaagc ctttcttgct ctttgatga agattttaca     120 gaagatcaat cacccagctt tcaacacctc tctaagcata accaaaattt tcttgctcgc     180
cttcatggca cccatttcta ccctgatacc tcaccgatga tgtctcaaag ccctgaatca     240
tcctggtctc cctctccttc gttaacccccc tctcatcctt ctcttctcta ctgctgtatc     300
tcctctctcc gtcgtgatgg tgatatttat tctctcactg tattcggtga cctagtctta     360
actggttcaa gtagtcgtcg agtctatgca tggcagtcac ttgactgcca tgcaaagggt     420
tacatacaat ctagctccgg cgaagtccgg gccatgcaag tctatgatga catgctcttc     480
actgcacata aggatcataa aattaggata tggaacatga aacttgcag tggtagcttt     540 agggctagaa aagtccttac cttaccttgt gctagccatt tcaagagttt catttgtagg     600
tctgttgtcc cacaccatag gttaactgct aataagccaa ttacaccaca acatagggat     660
attatctctt gcatggcttt ttactatgtt gaaagtattt tatacactgg ctcatttgat     720
aaaactatca agcttggaa gttaagtgta aagaagtgta tcgactcgtt tgtagctcat     780
ggtgaccaca tcaatgacat ggtggtcaac caacaaagtg gctaccttt tacttgttct     840 tcagatggaa cagtaaagat gtggttaagg gtttatggtg aacacagcca tgtccttatt     900
aaggtcttta gttttcatac ctacccctatt tatgccttgg ctttaggtgt gtcaccatca     960
caaaggagtt tcttgtattc cggatcttct gatggatgta taaatttctg ggtgcaagag    1020
atttctactc actacaatca cggtggagtc ttagaagggc atcagtttgc ggttctttgc    1080
ctagtgaccc tagataattt ggtgattagt gggtctgagg actcgacgat caggatttag    1140

<210> SEQ ID NO 3
<211> LENGTH: 482
<212> TYPE: PRT
<213> ORGANISM: Chenopodium quinoa

<400> SEQUENCE: 3

Met His Ala His Thr Lys Ile Ser Leu Val His Ile Ser Thr Pro Val
1               5                   10                  15

Phe Ser Leu Ala Met Asp Arg Gln Leu Ser His Lys Lys Ser Leu Ser
            20                  25                  30

Cys Phe Phe Asp Glu Asp Phe Thr Glu Asp Gln Ser Pro Ser Phe Gln
        35                  40                  45

His Leu Ser Lys His Asn Gln Asn Phe Leu Ala Arg Leu His Gly Thr
    50                  55                  60

His Phe Tyr Pro Asp Thr Ser Pro Met Met Ser Gln Ser Pro Glu Ser
65                  70                  75                  80

Ser Trp Ser Pro Ser Pro Ser Leu Thr Pro Ser His Pro Ser Leu Leu
                85                  90                  95

Tyr Cys Cys Ile Ser Ser Leu Arg Arg Asp Gly Asp Ile Tyr Ser Leu
```

```
                100             105             110
    Thr Val Phe Gly Asp Leu Val Leu Thr Gly Ser Ser Arg Arg Val
            115             120             125

Tyr Ala Trp Gln Ser Leu Asp Cys His Ala Lys Gly Tyr Ile Gln Ser
    130             135             140

Ser Ser Gly Glu Val Arg Ala Met Gln Val Tyr Asp Asp Met Leu Phe
    145             150             155             160

Thr Ala His Lys Asp His Lys Ile Arg Ile Trp Asn Met Arg Thr Cys
                165             170             175

Ser Gly Ser Phe Arg Ala Arg Lys Val Leu Thr Leu Pro Cys Ala Ser
                180             185             190

His Phe Lys Ser Phe Ile Cys Arg Ser Val Val Pro His Arg Leu
            195             200             205

Thr Ala Asn Lys Pro Ile Thr Pro Gln His Arg Asp Ile Ile Ser Cys
    210             215             220

Met Ala Phe Tyr Tyr Val Glu Ser Ile Leu Tyr Thr Gly Ser Phe Asp
    225             230             235             240

Lys Thr Ile Lys Ala Trp Lys Leu Ser Val Lys Cys Ile Asp Ser
                245             250             255

Phe Val Ala His Gly Asp His Ile Asn Asp Met Val Val Asn Gln Gln
                260             265             270

Ser Gly Tyr Leu Phe Thr Cys Ser Ser Asp Gly Thr Val Lys Met Trp
                275             280             285

Leu Arg Val Tyr Gly Glu His Ser His Val Leu Ile Lys Val Phe Ser
            290             295             300

Phe His Thr Tyr Pro Ile Tyr Ala Leu Ala Leu Gly Val Ser Pro Ser
    305             310             315             320

Gln Arg Ser Phe Leu Tyr Ser Gly Ser Ser Asp Gly Cys Ile Asn Phe
                325             330             335

Trp Val Gln Glu Ile Ser Thr His Tyr Asn His Gly Val Leu Glu
            340             345             350

Gly His Gln Phe Ala Val Leu Cys Leu Val Thr Leu Asp Asn Leu Val
            355             360             365

Ile Ser Gly Ser Glu Asp Ser Thr Ile Arg Ile Trp Arg Arg Glu Lys
            370             375             380

Val Arg Phe Thr His Glu Cys Leu Ala Val Leu Glu Gly His Arg Gly
    385             390             395             400

Pro Val Arg Cys Leu Ala Ala Ser Leu Gln Asp Glu Leu Val Thr Ser
                405             410             415

Phe Leu Val Tyr Ser Ala Ser Leu Asp Gln Thr Phe Lys Val Trp Arg
                420             425             430

Val Lys Leu Leu Arg Glu Val Lys Lys Ser Pro Gly Arg His Ser Asn
                435             440             445

Gly Asp Asp Asp Thr Glu Asp Thr Asn Ser Ala Gly Cys Glu Pro Ser
    450             455             460

Pro Val Leu Ser Pro Ser Trp Val Lys Lys Leu Gln Cys Arg Ser
    465             470             475             480

Leu Lys

<210> SEQ ID NO 4
<211> LENGTH: 1449
<212> TYPE: DNA
<213> ORGANISM: Chenopodium quinoa
```

<400> SEQUENCE: 4

```
atgcacgcac acacaaagat ttccctagtt cacatctcca ctcctgtttt ttctcttgcg      60
atggatcgcc agctcagtca caagaaaagc cttttcttgct tcttttgatga agattttaca    120
gaagatcaat cacccagctt tcaacacctc tctaagcata accaaaattt tcttgctcgc     180
cttcatggca cccatttcta ccctgatacc tcaccgatga tgtctcaaag ccctgaatca     240
tcctggtctc cctctccttc gttaaccccc tctcatcctt ctcttctcta ctgctgtatc     300
tcctctctcc gtcgtgatgg tgatatttat tctctcactg tattcggtga cctagtctta    360
actggttcaa gtagtcgtcg agtctatgca tggcagtcac ttgactgcca tgcaaaggt     420
tacatacaat ctagctccgg cgaagtccgg gccatgcaag tctatgatga catgctcttc    480
actgcacata aggatcataa aattaggata tggaacatga aacttgcag tggtagcttt     540
agggctagaa aagtccttac cttaccttgt gctagccatt tcaagagttt catttgtagg    600
tctgttgtcc cacaccatag gttaactgct aataagccaa ttacaccaca acatagggat    660
attatctctt gcatggcttt ttactatgtt gaaagtattt tatacactgg ctcatttgat    720
aaaactatca aagcttggaa gttaagtgta agaagtgta tcgactcgtt tgtagctcat     780
ggtgaccaca tcaatgacat ggtggtcaac caacaaagtg gctaccttt tacttgttct    840
tcagatggaa cagtaaagat gtggttaagg gtttatggtg aacacagcca tgtccttatt   900
aaggtcttta gttttcatac ctaccctatt tatgccttgg ctttaggtgt gtcaccatca   960
caaaggagtt tcttgtattc cggatcttct gatggatgta taaatttctg ggtgcaagag 1020
atttctactc actacaatca cggtggagtc ttagaagggc atcagtttgc ggttctttgc  1080
ctagtgaccc tagataattt ggtgattagt gggtctgagg actcgacgat caggatttgg 1140
aggcgagaga agtaagatt tactcatgag tgtcttgctg ttttagaagg gcatagaggg 1200
cctgtgagat gcttggctgc ttctttgcag gacgagcttg taacgagttt cttggtttat 1260
agtgctagct tggatcagac atttaaggtg tggagagtaa agctcttgcg agaagtgaag 1320
aaatcccctg ccgccatag caatggagat gatgatacgg aagatacaaa ttctgcaggg 1380
tgtgagccta gccctgtgtt gtctccttca tgggttaaga agaagcttca atgtcgtagt 1440
cttaaatag                                                          1449
```

<210> SEQ ID NO 5
<211> LENGTH: 294
<212> TYPE: PRT
<213> ORGANISM: Chenopodium quinoa

<400> SEQUENCE: 5

```
Lys Gly Tyr Ile Gln Ser Ser Ser Gly Glu Val Arg Ala Met Gln Val
1               5                   10                  15

Tyr Asp Asp Met Leu Phe Thr Ala His Lys Asp His Lys Ile Arg Ile
            20                  25                  30

Trp Asn Met Arg Thr Cys Ser Gly Ser Phe Arg Ala Arg Lys Val Leu
        35                  40                  45

Thr Leu Pro Cys Ala Ser His Phe Lys Ser Phe Ile Cys Arg Ser Val
    50                  55                  60

Val Pro His His Arg Leu Thr Ala Asn Lys Pro Ile Thr Pro Gln His
65                  70                  75                  80

Arg Asp Ile Ile Ser Cys Met Ala Phe Tyr Tyr Val Glu Ser Ile Leu
                85                  90                  95

Tyr Thr Gly Ser Phe Asp Lys Thr Ile Lys Ala Trp Lys Leu Ser Val
```

```
            100                 105                 110
Lys Lys Cys Ile Asp Ser Phe Val Ala His Gly Asp His Ile Asn Asp
            115                 120                 125

Met Val Val Asn Gln Gln Ser Gly Tyr Leu Phe Thr Cys Ser Ser Asp
            130                 135                 140

Gly Thr Val Lys Met Trp Leu Arg Val Tyr Gly Glu His Ser His Val
145                 150                 155                 160

Leu Ile Lys Val Phe Ser Phe His Thr Tyr Pro Ile Tyr Ala Leu Ala
            165                 170                 175

Leu Gly Val Ser Pro Ser Gln Arg Ser Phe Leu Tyr Ser Gly Ser Ser
            180                 185                 190

Asp Gly Cys Ile Asn Phe Trp Val Gln Glu Ile Ser Thr His Tyr Asn
            195                 200                 205

His Gly Gly Val Leu Glu Gly His Gln Phe Ala Val Leu Cys Leu Val
            210                 215                 220

Thr Leu Asp Asn Leu Val Ile Ser Gly Ser Glu Asp Ser Thr Ile Arg
225                 230                 235                 240

Ile Trp Arg Arg Glu Lys Val Arg Phe Thr His Glu Cys Leu Ala Val
                    245                 250                 255

Leu Glu Gly His Arg Gly Pro Val Arg Cys Leu Ala Ala Ser Leu Gln
            260                 265                 270

Asp Glu Leu Val Thr Ser Phe Leu Val Tyr Ser Ala Ser Leu Asp Gln
            275                 280                 285

Thr Phe Lys Val Trp Arg
            290

<210> SEQ ID NO 6
<211> LENGTH: 241
<212> TYPE: PRT
<213> ORGANISM: Chenopodium quinoa

<400> SEQUENCE: 6

Lys Gly Tyr Ile Gln Ser Ser Ser Gly Glu Val Arg Ala Met Gln Val
1               5                   10                  15

Tyr Asp Asp Met Leu Phe Thr Ala His Lys Asp His Lys Ile Arg Ile
            20                  25                  30

Trp Asn Met Arg Thr Cys Ser Gly Ser Phe Arg Ala Arg Lys Val Leu
        35                  40                  45

Thr Leu Pro Cys Ala Ser His Phe Lys Ser Phe Ile Cys Arg Ser Val
    50                  55                  60

Val Pro His His Arg Leu Thr Ala Asn Lys Pro Ile Thr Pro Gln His
65                  70                  75                  80

Arg Asp Ile Ile Ser Cys Met Ala Phe Tyr Tyr Val Glu Ser Ile Leu
            85                  90                  95

Tyr Thr Gly Ser Phe Asp Lys Thr Ile Lys Ala Trp Lys Leu Ser Val
            100                 105                 110

Lys Lys Cys Ile Asp Ser Phe Val Ala His Gly Asp His Ile Asn Asp
            115                 120                 125

Met Val Val Asn Gln Gln Ser Gly Tyr Leu Phe Thr Cys Ser Ser Asp
            130                 135                 140

Gly Thr Val Lys Met Trp Leu Arg Val Tyr Gly Glu His Ser His Val
145                 150                 155                 160

Leu Ile Lys Val Phe Ser Phe His Thr Tyr Pro Ile Tyr Ala Leu Ala
            165                 170                 175
```

-continued

```
Leu Gly Val Ser Pro Ser Gln Arg Ser Phe Leu Tyr Ser Gly Ser Ser
            180                 185                 190

Asp Gly Cys Ile Asn Phe Trp Val Gln Glu Ile Ser Thr His Tyr Asn
        195                 200                 205

His Gly Gly Val Leu Glu Gly His Gln Phe Ala Val Leu Cys Leu Val
    210                 215                 220

Thr Leu Asp Asn Leu Val Ile Ser Gly Ser Glu Asp Ser Thr Ile Arg
225                 230                 235                 240

Ile

<210> SEQ ID NO 7
<211> LENGTH: 300
<212> TYPE: DNA
<213> ORGANISM: Chenopodium quinoa

<400> SEQUENCE: 7
atgcacgcac acacaaagat ttccctagtt cacatctcca ctcctgtttt ttctcttgcg      60
atggatcgcc agctcagtca caagaaaagc ctttcttgct tctttgatga agattttaca    120
gaagatcaat cacccagctt tcaacacctc tctaagcata accaaaattt tcttgctcgc    180
cttcatggca cccatttcta ccctgatacc tcaccgatga tgtctcaaag ccctgaatca    240
tcctggtctc cctctccttc gttaaccccc tctcatcctt ctcttctcta ctgctgtatc    300
```